US007771358B2

(12) United States Patent
Moehring et al.

(10) Patent No.: US 7,771,358 B2
(45) Date of Patent: Aug. 10, 2010

(54) SYSTEM AND METHOD FOR GRADING MICROEMBOLI MONITORED BY A MULTI-GATE DOPPLER ULTRASOUND SYSTEM

(75) Inventors: Mark A. Moehring, Seattle, WA (US); Asanka S. Dewaraja, Federal Way, WA (US); Thomas O. Mera, Bellevue, WA (US); Merrill P. Spencer, Seattle, WA (US)

(73) Assignee: Spentech, Inc., Seattle, WA (US)

( * ) Notice: Subject to any disclaimer, the term of this patent is extended or adjusted under 35 U.S.C. 154(b) by 571 days.

(21) Appl. No.: 11/134,862

(22) Filed: May 20, 2005

(65) Prior Publication Data

US 2006/0264759 A1    Nov. 23, 2006

(51) Int. Cl.
*A61B 8/00*   (2006.01)
*A61B 8/14*   (2006.01)

(52) U.S. Cl. .................. 600/454; 600/455; 600/457; 600/469

(58) Field of Classification Search .......... 600/454, 600/437, 453, 523, 438, 455, 457–458, 469; 128/647
See application file for complete search history.

(56) References Cited

U.S. PATENT DOCUMENTS

| | | | |
|---|---|---|---|
| 4,014,206 A | 3/1977 | Taylor | 73/19 |
| 4,015,464 A * | 4/1977 | Miller et al. | 73/61.75 |
| 4,152,928 A | 5/1979 | Roberts | 73/61 R |
| 4,276,491 A | 6/1981 | Daniel | 310/317 |
| 4,319,580 A | 3/1982 | Colley et al. | 128/661 |
| 4,501,277 A | 2/1985 | Hongo | 128/660 |
| 4,537,074 A | 8/1985 | Dietz | 73/625 |
| 4,751,929 A | 6/1988 | Hayakawa et al. | 128/663 |
| 4,800,891 A | 1/1989 | Kim | 128/661.09 |

(Continued)

FOREIGN PATENT DOCUMENTS

AU   765304   *   1/2004

(Continued)

OTHER PUBLICATIONS

Zagzebski, James A., "Essentials of Ultrasound Physics", Mosby, Inc., St. Louis, Missouri, 1996. pp. 46-68 and 109-122.

(Continued)

*Primary Examiner*—Eric F Winakur
*Assistant Examiner*—Katherine L Fernandez
(74) *Attorney, Agent, or Firm*—Dorsey & Whitney LLP

(57) ABSTRACT

Systems and methods for grading signals from microemboli in blood flow monitored using a Doppler ultrasound system. Signals from microemboli in blood flow are graded by calculating a value related to a power for the signals from microemboli in blood flow and categorizing the signals into one of at least two grades based on the calculated value. Alternatively, signals can be categorized by assessing a power value for the microemboli in blood flow during a period of monitoring. In response to the power value being greater than or equal to a threshold value, the microemboli in blood flow are categorized based on the power value, and in response to the power value being less than the threshold value, a number of microemboli are counted during at least a portion of the period of monitoring and the microemboli are categorized based on the number.

23 Claims, 11 Drawing Sheets

U.S. PATENT DOCUMENTS

| | | | |
|---|---|---|---|
| 4,848,354 A | 7/1989 | Angelsen et al. | 128/660.05 |
| 4,896,674 A | 1/1990 | Seo | 128/661.09 |
| 4,932,415 A | 6/1990 | Angelsen et al. | 128/661.09 |
| 4,993,417 A | 2/1991 | Seo | 128/661.09 |
| 4,993,418 A | 2/1991 | Weaver et al. | 128/661.08 |
| 5,053,008 A | 10/1991 | Bajaj | 604/104 |
| 5,083,567 A | 1/1992 | Uchibori | 128/661.09 |
| 5,101,828 A | 4/1992 | Welkowitz et al. | 128/668 |
| 5,103,826 A | 4/1992 | Bonnefous | 128/661.08 |
| 5,103,827 A * | 4/1992 | Smith | 600/454 |
| 5,129,399 A | 7/1992 | Hirama | 128/661.01 |
| 5,148,808 A | 9/1992 | Satake | 128/660.05 |
| 5,190,044 A | 3/1993 | Kawasaki et al. | 128/661.09 |
| 5,231,573 A | 7/1993 | Takamizawa | 364/413.25 |
| 5,249,577 A | 10/1993 | Shinomura et al. | 128/660.05 |
| 5,271,404 A | 12/1993 | Corl et al. | 128/661.08 |
| 5,348,015 A * | 9/1994 | Moehring et al. | 600/453 |
| 5,441,051 A | 8/1995 | Hileman et al. | 128/661.08 |
| 5,476,097 A | 12/1995 | Robinson | 128/660.05 |
| 5,501,223 A | 3/1996 | Washburn et al. | 128/661.09 |
| 5,513,640 A | 5/1996 | Yamazaki et al. | 128/661.09 |
| RE35,371 E | 11/1996 | Seo | 128/661.09 |
| 5,590,658 A | 1/1997 | Chiang et al. | 128/661.01 |
| 5,615,680 A | 4/1997 | Sano | 128/661.09 |
| 5,622,173 A | 4/1997 | Bisson et al. | 128/661.01 |
| 5,722,412 A | 3/1998 | Pflugrath et al. | 128/662.03 |
| 5,732,705 A | 3/1998 | Yokoyama et al. | 128/660.07 |
| 5,785,654 A | 7/1998 | Iinuma et al. | 600/441 |
| 5,785,655 A | 7/1998 | Goodsell, Jr. et al. | 600/441 |
| 5,800,356 A | 9/1998 | Criton et al. | 600/441 |
| 5,833,615 A | 11/1998 | Wu et al. | 600/458 |
| 5,860,927 A | 1/1999 | Sakaguchi et al. | 600/453 |
| 5,882,315 A | 3/1999 | Ji et al. | 600/553 |
| 5,910,118 A | 6/1999 | Kanda et al. | 600/455 |
| 5,913,824 A | 6/1999 | Ogasawara et al. | 600/455 |
| 5,919,139 A | 7/1999 | Lin | 600/443 |
| 5,924,991 A | 7/1999 | Hossack et al. | 600/443 |
| 5,947,904 A | 9/1999 | Hossack et al. | 600/458 |
| 5,997,478 A | 12/1999 | Jackson et al. | 600/437 |
| 6,045,505 A | 4/2000 | Holley et al. | 600/441 |
| 6,196,972 B1 | 3/2001 | Moehring | 600/454 |
| 6,468,219 B1 | 10/2002 | Njemanze | 600/454 |
| 6,482,161 B1 | 11/2002 | Sumanaweera et al. | 600/454 |
| 6,503,202 B1 | 1/2003 | Hossack et al. | 600/454 |
| 6,524,249 B2 | 2/2003 | Moehring et al. | 600/438 |
| 6,547,732 B2 | 4/2003 | Jago | 600/437 |
| 6,547,736 B1 | 4/2003 | Moehring et al. | 600/454 |
| 6,616,611 B1 | 9/2003 | Moehring | 600/454 |
| 6,629,449 B1 | 10/2003 | Kline-Schoder et al. | 73/19.03 |
| 6,635,017 B1 | 10/2003 | Moehring et al. | 600/439 |
| 7,128,713 B2 * | 10/2006 | Moehring et al. | 600/453 |
| 7,537,568 B2 | 5/2009 | Moehring | 600/454 |
| 2002/0091319 A1* | 7/2002 | Moehring et al. | 600/454 |
| 2004/0019278 A1 | 1/2004 | Abend | 600/454 |
| 2004/0138563 A1 | 7/2004 | Moehring et al. | 600/439 |
| 2005/0033174 A1 | 2/2005 | Moehring et al. | 600/453 |
| 2005/0075568 A1 | 4/2005 | Moehring | 600/453 |
| 2005/0101863 A1 | 5/2005 | Kawagishi et al. | 600/443 |
| 2005/0251041 A1 | 11/2005 | Moehring | 600/441 |
| 2007/0016050 A1 | 1/2007 | Moehring et al. | 600/454 |

FOREIGN PATENT DOCUMENTS

| | | | |
|---|---|---|---|
| EP | 0 079 453 A1 * | 5/1983 | |
| EP | 0 164 835 B1 * | 1/1989 | |
| EP | 1 182 452 A2 * | 2/2002 | |
| EP | 1182452 A2 | 2/2002 | |
| JP | 2002-52913 * | 2/2002 | |
| TW | 2005-18718 * | 6/2005 | |
| TW | 2006-12869 * | 5/2006 | |
| TW | 2007-01954 * | 1/2007 | |
| WO | 94/06353 A2 * | 3/1994 | |
| WO | WO 96/21215 | 7/1996 | |
| WO | 00/27288 * | 5/2000 | |
| WO | 2005/006952 A2 * | 1/2005 | |
| WO | 2005/112771 A2 * | 12/2005 | |
| WO | 2006/127542 A2 * | 11/2006 | |
| WO | 2006/138185 A2 * | 12/2006 | |
| WO | 2007/022055 A1 * | 2/2007 | |

OTHER PUBLICATIONS

*Aloka-860 Operational Manual.* vol. I System Description, Effective S/N: 51M8876 and above. pp. i-15-2 and A-2-A-5.

*Aloka Color Doppler Model SSD-860 Cardiovascular Scanner* Sales Brochure. Aloka Co., Ltd., Japan.

Demchuk, A.M. et al., "Thrombolysis in Brain Ischemia (TIBI) Transcranial Doppler Flow Grades Predict Clinical Severity, Early Recovery, and Mortality in Patients Treated with Intravenous Tissue Plasminogen Activator", American Heart Association, Inc., Jan. 2001. pp. 89-93.

Duncan, Walter J. *Color Doppler in Clinical Cardiology.* Philadelphia, W.B. Saunders Company, Harcourt Brace Jovanovich, Inc., 1988. pp. 1-13.

Ferrera, K. et al., "Color Flow Mapping," Ultrasound in Medicine and Biology, vol. 23, No. 3, 1997, pp. 321-345.

Giller, C.A. et al., "Oscillations in Cerebral Blood Flow Detected with a Transcranial Doppler Index", Journal of Cerebral Blood Flow and Metabolism, vol. 19, No. 4, Apr. 1999. pp. 452-459.

Griffith, James M. et al., "An Ultrasound System for Combined Cardiac Imaging and Doppler Blood Flow Measurement in Man", Biomedical Engineering and Instrumentation Branch, Division of Research Services and the Cardiology Branch, National Heart, Lung, and Blood Institute, Maryland, vol. 57, No. 5, May 1978, pp. 925-930.

Iwase, Masatsugu et al. *Clinical Echocardiography.* Dordrecht, Kluwer Academic Publishers, 1989. pp. 11-27 and 250-281.

Kremkau, G.W. *Doppler Ultrasound, Principles and Instruments.* (Philadelphia, W.B. Saunders Company, 1990), pp. 177-211.

Missri, José*Clinical Doppler Echocardiography Spectral and Color Flow Imaging.* New York, McGraw-Hill, Inc., 1990. pp. 9-27 and 279-303.

Omoto, R. et al., "The Development of Real-Time Two-Dimensional Doppler Echocardiography and Its Clinical Significance in Acquired Valvular Diseases With Special Reference to the Evaluation of Valvular Regurgitation", Reprinted from *Japanese Heart Journal,* vol. 25, No. 3, pp. 325-340, May 1984.

Omoto, R. et al., "Clinical Significance and Prospects of Real-Time Two-Dimensional Doppler Echocardiography", Color ATLAS of Real-Time Two-Dimensional Doppler Echocardiography, Chapter 1-6, pp. 1-44, Shindan-To-Chiryo Co., Ltd. Tokyo 1984.

"Operation Manual for Diagnostic Ultrasound Equipment Model SSH-160A (2B730-405E*B)", Toshiba Corporation, 1987, pp. 7-4-7-5, 8-1, 11-1-11-3, 11-12, 12-1, 12-3 and 16-10.

Redel, Dierk A. *Color Blood Flow Imaging of the Heart.* Germany, Springer-Verlag Berlin Heidelberg, 1988. pp. 5-12 and 27-41.

Weyman, Arthur E. *Principles and Practice of Echocardiography,* 2d ed. Philadelphia, Lea & Febiger, 1994. pp. 218-233 and 256-281.

Moehring, M.A. et al., "Power M-Mode Doppler (PMD) for Observing Cerebral Blood Flow and Tracking Emboli", Ultrasound in Medicine and Biology, vol. 28, No. 1, 2002. pp. 49-57.

Kisslo J.A., et al., "Color Flow Imaging", Echo inContext, Duke Center for Echo, www.echoincontext.com/doppler04/doppler04_01.asp, Duke University Medical Center, 2000. 30 pages.

Alexandrov, A.V. et al., "Insonation Method and Diagnostic Flow Signatures for Transcranial Power Motion (M-Mode) Doppler", Journal of Neuroimaging, vol. 12, No. 3, Jul. 2002. pp. 236-244.

* cited by examiner

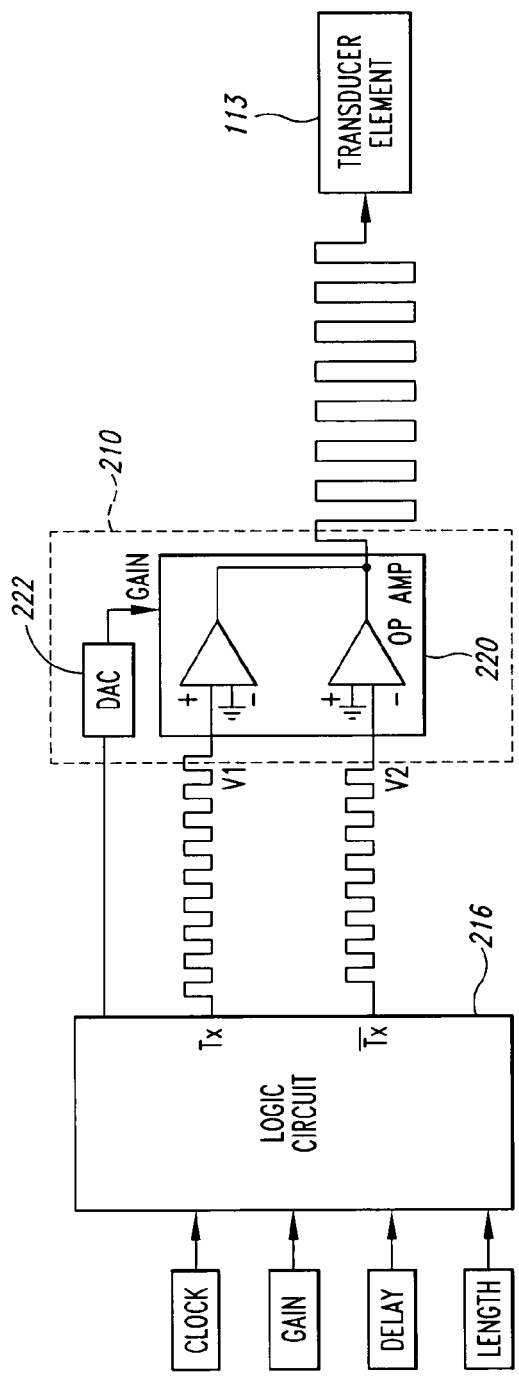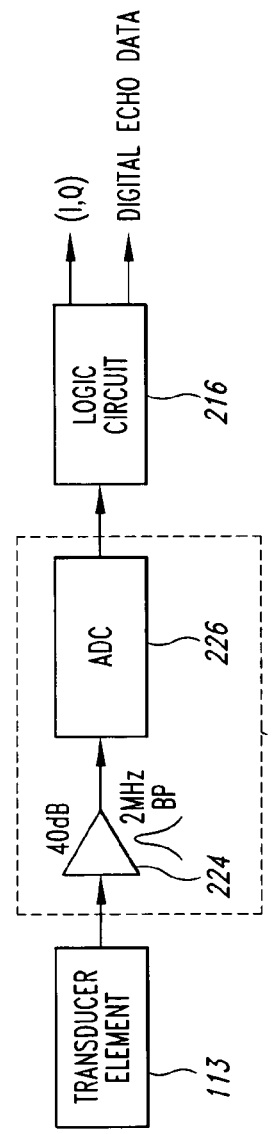
Fig. 3A
Fig. 3B

1

2

3

4

5

5+

SYSTEM AND METHOD FOR GRADING MICROEMBOLI MONITORED BY A MULTI-GATE DOPPLER ULTRASOUND SYSTEM

TECHNICAL FIELD

The invention relates generally to Doppler ultrasound systems, and more particularly, a system and method for grading microemboli, such as ultrasonic contrast agents that move in blood flow, using a multi-gate Doppler ultrasound system.

BACKGROUND OF THE INVENTION

Cryptogenic strokes and transient ischemic attacks ("TIAs") are those in which no obvious cause is found by patient history, carotid Doppler studies, or cardiac conditions such as atrial fibrillation, myocardial infarction, or valve diseases. Patent foramen ovale ("PFO"), which is a small flap-valve hole in the heart, has been associated with cryptogenic stroke allowing paradoxical embolism from the veins to the brain through a right-to-left shunt ("RLS"). Normally, blood returning to the heart from the veins is re-oxygenated when it is pumped from the right side of the heart and then through the lungs. However, in people with PFO, the venous blood, which may contain clots, may instead travel through the hole (i.e., the PFO) between the upper chambers of the heart and into the arterial blood, bypassing the lungs where the clots would normally be filtered out. When this blood goes to the brain, a clot may cause a stroke or stroke-like symptoms. In approximately 40 percent of stroke cases, the underlying cause is difficult to determine and the stroke is called "cryptogenic". Evidence now suggests that when a person has a stroke, and its cause is undetermined, the person is about twice as likely as the normal population to have PFO.

Currently, PFO is considered when stroke occurs in young people. However, PFO is found in all ages; 34% of adults in the first three decades of life declining to 20% in the 9th and 10th decades and ranging from 1 to 19 mm in diameter. Cryptogenic stroke patients, assessed with traditional single gate transcranial Doppler ("sgTCD"), have 12 to 1 odds of having a large PFO compared to a non-stroke group. Also, migraine patients with aura have a 3 to 1 odds of having a PFO compared to a non-migraine group. Conditions for venous thrombosis and pulmonary embolism also exist widely and deep vein thrombosis is a common finding in the vascular laboratory. Therefore, the conditions for paradoxical embolism are widely prevalent at all ages.

Atrial septal defect ("ASD") is a permanent opening through the interatrial septum that often persists into adulthood. Blood flows back and forth through the defect depending on the back and forth pressure gradient between the atria. This defect usually places a load on the right ventricle that, however, may be tolerated for many years. If the mean right atrial pressure is chronically elevated these patients have a significant desaturation of the arterial blood.

The urgency to diagnose PFO and ASD is driven by the advent of safe transcatheter closure devices and the popularity of TCD over invasive transesophageal echocardiography ("TEE") has enhanced the search for PFO and ASD. sgTCD has demonstrated high accuracy in ruling in, and ruling out, PFO when compared to TEE. Particularly, sgTCD is able to detect large shunts, which are more clinically relevant. Using intravenous injections of agitated saline, which provide an ultrasonic contrast agent of bubbles, the suspended bubbles pass through the PFO from the right to the left atrium and are easily detected by TCD as audible chirps and microembolic spectra in the cerebral arteries. Agitated saline contrast agent has been used safely for many years in echocardiography and TCD. As known, bubbles in agitated saline do not pass the lungs, and therefore a shunt from the venous system to the arterial system which bypasses the lungs is the only way for bubbles to be seen on the arterial side. A Valsalva strain (forced expiratory effort against a closed glottis) facilitates passage of the microbubbles through the PFO by raising the pressure in the right atrium over that of the left atrium.

TEE is currently considered the "gold standard" for PFO diagnosis. However, it is poorly tolerated by patients and requires deep sedation, which limits the patient's ability to perform a Valsalva maneuver. sgTCD has proven to be a reliable technique for diagnosing PFO. While PFO diagnosis and treatment are facilitated by TCD's less invasive technology, sgTCD and TEE are limited by a grading system that uses 3 categories to rate the degree of RLS. In patients with ischemic or cryptogenic stroke, the need exists to further quantify RLS.

An improvement over the use of TEE and sgTCD for evaluating PFO is provided by recently developed multi-gate power m-mode TCD (pmTCD) ultrasound devices. An example of such an ultrasound system is the digital Doppler platform developed by Spencer Technologies in Seattle, Wash. in which up to 33 sample gates placed at 2 mm intervals can be simultaneously processed into a "color" power m-mode image. The color in the m-mode image is a function of Doppler signature power and detected velocity, in that increases in backscattered power cause the colors, red or blue, to become more intense. Additionally, a spectrogram for a selected depth in the depth range can be displayed. The digital Doppler platform is referred to as Spencer Technologies' Power M-mode Doppler ("PMD"). Showing power in this fashion conveys to the user when the Doppler beam is well aimed—that is, intensity of color increases with volume of moving blood in the Doppler sample volume and this indicates when the beam is centered on the blood flow. Thus, the color m-mode display of an ultrasound system having PMD capability provides medical professionals who do not have expertise in ultrasound with a mechanism for easy location (by the operator) of the middle cerebral circulation. A more detailed description of PMD ultrasound systems can be found in U.S. Pat. No. 6,196,972 to Moehring, issued Mar. 6, 2001 and assigned to Spencer Technologies.

In an application evaluating PFO, pmTCD detects 66% more bubble microemboli than traditional sgTCD. The increased detectability allows for use of an expanded six-level grading scale to rate the degree of RLS, in contrast to the three-level grading system provided by TEE and sgTCD. In performing the evaluation of PFO using pmTCD, bilateral monitoring is performed with the beam including the ipsilateral middle cerebral and anterior cerebral arteries ("MCAs") and ("ACAs"). The two probes are positioned bilaterally and stabilized using a head-frame worn by the patient. The spectrogram sample volumes of the PMD are set near the origin of each respective MCA at a depth of 50 mm to 60 mm. The PMD is observed for embolic tracks ("ETs") while listening to the MCA spectral signal.

In observing the bubble emboli, pmTCD produces unique signatures of emboli, appearing as brightly colored ETs as they pass through the insonated arteries. When an embolus moves toward the transducer, a bright red upward-sloping ET is produced. In contrast, when an embolus moves away from the transducer, a bright blue downward-sloping ET is produced. The sloping feature of the ET is prima facie evidence of an embolus (i.e., a bubble or particle) carried by the blood through a vessel within the ultrasound beam. The slope shows the embolus velocity as a change in depth over time. If the single gate is placed in any of the colored bands, ETs also appear on the spectrogram as high intensity microembolic signals ("MESs").

For PFO evaluation, generally, all ETs are counted in the bilaterally insonated arteries from a depth range of approximately 40 mm to 75 mm. Typically, all ETs and MESs are counted visually. Because the beams overlap at the midline at a depth of 75 mm, ETs are not counted at depths beyond 75 mm. Based on the number of ETs counted, a grade is determined according to following the expanded six-level logarithmic grading scale to rate the degree of RLS: grade 0=0 ETs, grade I=1-10 ETs, grade II=11-30 ETs, grade III=31-100 ETs, grade IV=101-300 ETs, and grade V>300 ETs. The expanded six-level grading scale does not predict the size of the opening, but does provide a measure of the conductance or ability of the opening to transmit material from the venous circulation to the brain. That is, the numbers of ETs represent tracers of the conductance of RLS flow to the anterior circulation of the brain. The conductance takes into account many factors including the RLS flow distribution to the anterior circulation of the brain, the size of the foramen while open, and the right-to-left pressure gradient when the foramen is open. For unilateral pmTCD monitoring, the number of ETs counted are doubled and the resulting number applied to the six-level grading scale accordingly.

The use of pmTCD has provided greater accuracy and an improved grading scale for determining the functional conductance of PFO. However, the process of visually counting the ETs detected during examination can be time consuming. Thus, immediate grading of PFO for the higher grades is unlikely. Additionally, counting the number of ETs for the higher grades, such as grades 4 and above, is often difficult as visually distinguishing between individual ETs on a PMD monitor for higher grades, that is, those grades having higher number and density of ETs, may not be possible. As a result, the grading process, specifically for PFO, and more generally, for any visual counting or grading process based on the number of ETs, is susceptible to counting errors. Moreover, due to the practical limitations of visually counting individual ETs at higher densities of ETs, further expansion of a grading scale to provide greater grading resolution may not be possible.

SUMMARY OF THE INVENTION

Aspects of the invention include systems and methods for grading signals from microemboli in blood flow that is monitored using a Doppler ultrasound system. In one aspect, the signals from microemboli in blood flow are graded by calculating a value related to a power for the signals from microemboli in blood flow and categorizing the signals from microemboli in blood flow into one of at least two grades based on the calculated value. In another aspect of the invention, categorizing microemboli in blood flow monitored using a Doppler ultrasound system includes assessing a power value for the microemboli in the blood flow during a period of monitoring. In response to the power value being greater than or equal to a threshold value, categorizing the microemboli in blood flow based on the power value, and in response to the power value being less than the threshold value, counting a number of microemboli during at least a portion of the period of monitoring and categorizing the microemboli based on the number.

BRIEF DESCRIPTION OF THE DRAWINGS

FIG. 3A is a functional block diagram of a transmit circuit of the DSP platform of FIG. 2. FIG. 3B is a functional block diagram of a receive circuit of the DSP platform of FIG. 2.

DETAILED DESCRIPTION OF PREFERRED EMBODIMENTS

The present invention includes embodiments directed to automatically grading and/or counting embolic signatures detected using a multi-gate Doppler ultrasound system. One embodiment of the present invention, which will be described in more detail below, can be used with a multi-gate pmTCD ultrasound device for grading the functional conductance of PFO. Alternative embodiments of the present invention can also be used in other applications where grading and/or counting ETs during monitoring cerebral blood flow using pmTCD is desirable, including, monitoring the brain during heart surgery, carotid surgery, orthopedic surgery, or other procedure where significant invasive activity may potentially release emboli returning to the heart in the venous system. Certain details are set forth below to provide a sufficient understanding of the invention. However, it will be clear to one skilled in the art that the invention may be practiced without these particular details. Moreover, the particular embodiments of the present invention described herein are provided by way of example and should not be used to limit the scope of the invention to these particular embodiments. In other instances, well-known circuits, control signals, timing protocols, and software operations have not been shown in detail in order to avoid unnecessarily obscuring the invention.

Figure 1:
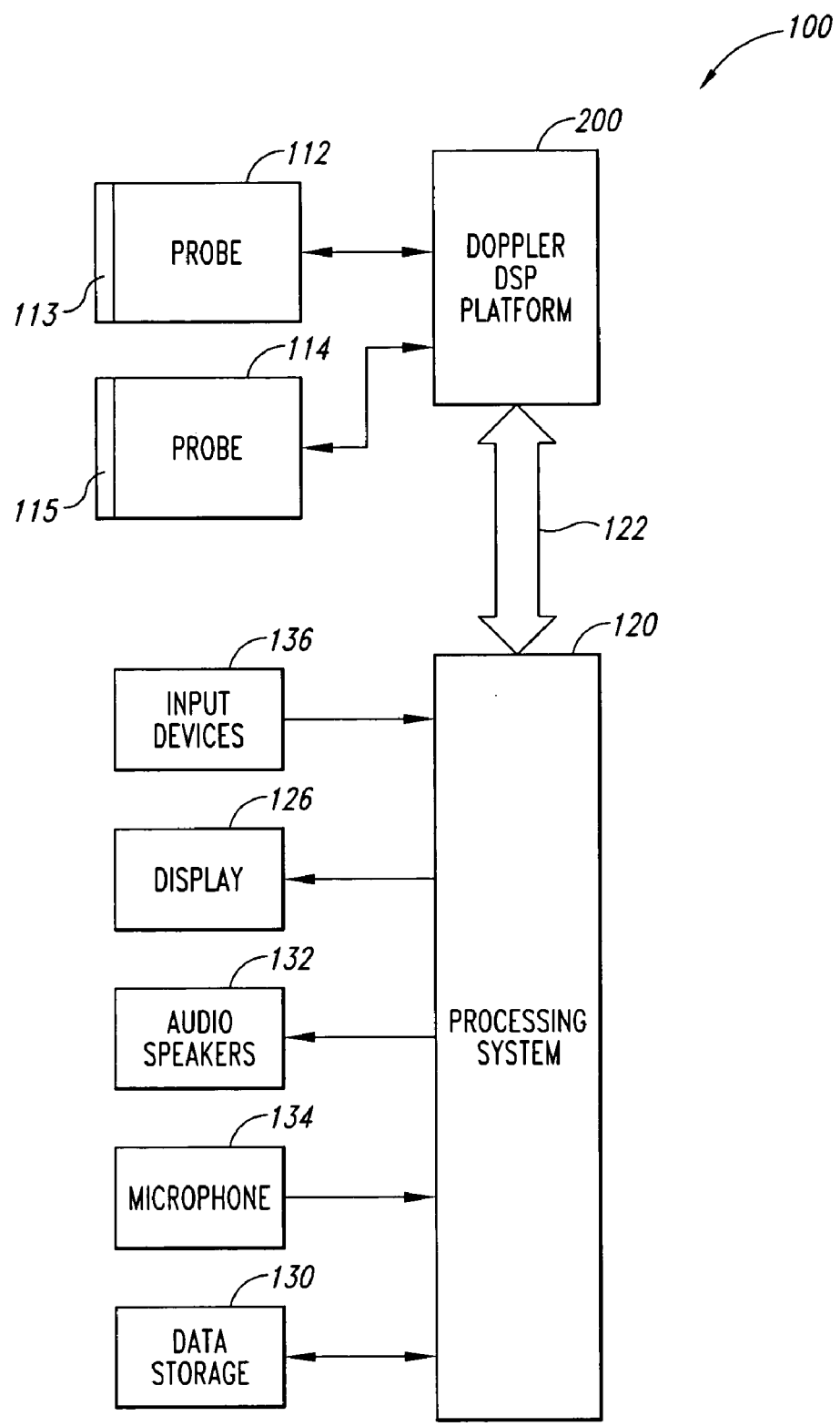
FIG. 1 is a functional block diagram of a Doppler ultrasound system in which embodiments of the present invention can be implemented.

FIG. 1 is a functional block diagram of a multi-gate Doppler ultrasound system 100 in which an embodiment of the present invention can be implemented. The ultrasound system 100 includes a Doppler DSP platform 200 coupled to a probe 112 having an ultrasound transducer 113. The Doppler DSP platform 200 provides for generating transmit waveforms to drive the transducer of the probe 112, digitizing echo signals detected by the transducer 113 of the probe 112, and signal processing to generate Doppler shift data representative of Doppler shift signals extracted from the echo signals.

As shown in FIG. 1, a second probe 114 having an ultrasound transducer 115 can also be coupled to the DSP 200 where bilateral monitoring of cerebral blood flow is desirable. The probe 114 can be the same in structure and functionality as the probe 112 previously described. Consequently, a more detailed description of the probe 114 has not been provided herein. When using both the probes 112, 114 for monitoring blood flow, the Doppler DSP platform 200 is further capable of controlling the transmit function of both the probes, as well as process the echo signals detected by the probes 112, 114 in order to generate Doppler shift data representing Doppler shift signals extracted from the echo signals. In one embodiment, a separate channel is provided for each probe 112, 114. In an alternative embodiment, various circuits are shared between the two channels while other circuits are kept separate. It will be appreciated by those ordinarily skilled in the art that the particular arrangement of the circuits described herein are not intended to limit the scope of the present invention.

The DSP platform 200 is coupled to a processing system 120 through a bus 122. The bus 122 can be implemented using conventional computer busses and protocols, for example, the bus 122 can be a universal serial bus ("USB"). The processing system 120 is configured for additional processing of Doppler shift data provided by the DSP platform 200. The processing system 120 also provides the DSP platform 200 with, among other things, commands and data for controlling the functions of the DSP platform 200. Additionally, the processing system 120 executes a grading algorithm for grading and/or counting ETs detected by the ultrasound system 100, as described in more detail below. The processing system 120 can be a host computer system to which the DSP platform 200 is coupled, or alternatively, can represent processing systems included with the DSP platform 200, or in an ultrasound system in which the DSP platform 200 is included for standalone Doppler processing.

The processing system 120 is coupled to a display device 126 for providing visual information and feedback to an operator. The information can be displayed in different formats on the display device 126. For example, in a specific application for monitoring cerebral blood flow, blood flow information can be displayed in a PMD format, as described in U.S. Pat. No. 6,196,972 to Moehring, which is incorporated herein by reference. The display device 126 can be a conventional display device now known or later developed, including a flat panel display or cathode ray tube ("CRT") display, which can be integrated with the ultrasound system 100, or is a standalone display device connected to the processing system 120.

The processing system 120 is further coupled to a data storage device 130 to store data or retrieve data from external storage media. Examples of typical data storage devices 130 include hard and floppy disks, tape cassettes, compact disk read-only ("CD-ROMs") and compact disk read-write ("CD-RW") memories, and digital video disks ("DVDs"). The ultrasound system 100 is also coupled to audio speakers 132 for providing audio information, and is further coupled to a microphone 134 for receipt of audible information input by an operator. One or more input devices 136, such as a keyboard or a mouse, are included in the ultrasound system 100 to allow the operator to interface with the ultrasound system 100. Although not shown in FIG. 1, the processing system 120 can further include conventional circuits and software for storing the audio and visual information for later playback and viewing.

Figure 2:
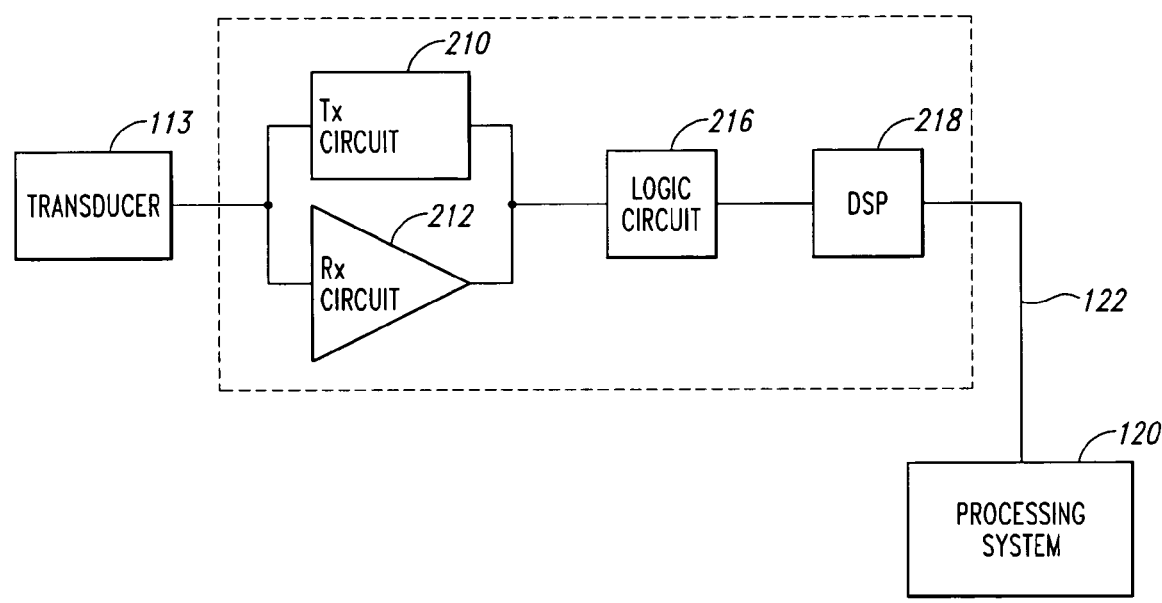
FIG. 2 is a functional block diagram of a portion of a Doppler digital signal processor ("DSP") platform of the Doppler ultrasound system of FIG. 1.
Figure 4:
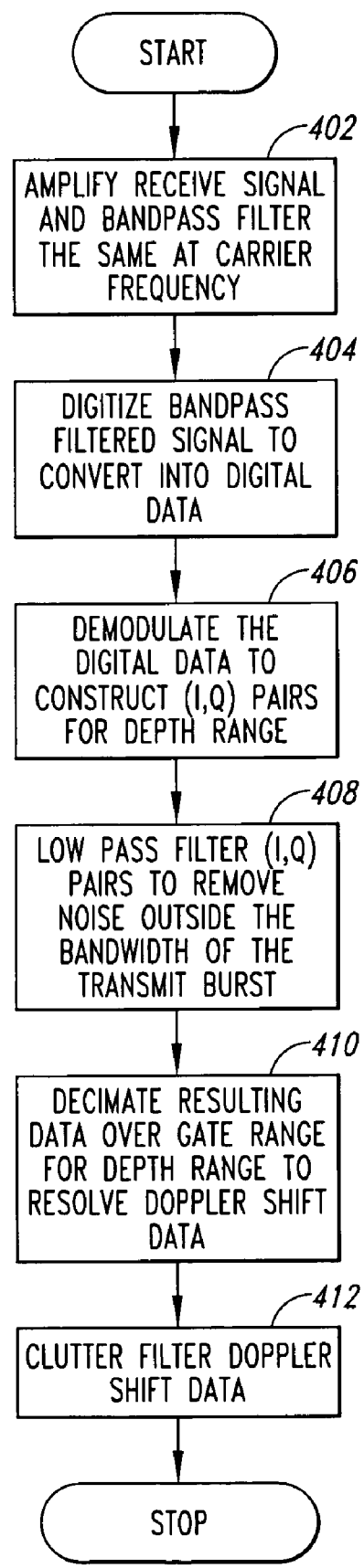
FIG. 4 is a flow diagram for Doppler shift signal processing performed by the DSP platform of FIG. 2.

FIG. 2 illustrates a portion of the circuits included in the DSP platform 200. The DSP platform 200 includes a TX/RX/DSP-channel 201 coupled to the transducer 113 of the probe 112. The TX/RX/DSP-channel 201 includes transmit and receive circuits 210 and 212, respectively, coupled to a DSP 218 through a logic circuit 216. The logic circuit 216 represents a front end processor that is used for performing repetitive tasks in the processing chain and provides a link between the analog front end of the TX/RX/DSP-channel 201 represented by the transmit and receive circuits 210 and 212, and the digital environment of the DSP 218. The TX/RX/DSP-channel 201 is coupled through the data bus 122 to the processing system 120. As previously discussed, the processing system 120 can represent a host computer system, processing systems included with the DSP platform 200, processing systems included in the ultrasound system 100, or some other alternative processing system. Where the probe 114 is used in combination with the probe 112 for bilateral monitoring, as previously discussed, a second TX/RX/DSP-channel (not shown, the same as the TX/RX/DSP-channel 201) can be included in the DSP platform 200.

FIGS. 3A and 3B illustrate the transmit circuit 210 and the receive circuit 212, respectively, that are included in the TX/RX/DSP-channel 201 (FIG. 2). The transmit and receive circuits 210, 212 are coupled to the ultrasound transducer 113 of the probe 112 to provide transmit and receive functionality, respectively, to the probe 112. With reference to FIG. 3A, the transmit circuit 210 receives control signals from the processing system 120 to control the ultrasound beam delivered by the prove 112. For example, the control signals provided to the transmit circuit 210 can be used to set gain, carrier frequency, length of the transmit burst and pulse repetition frequency ("PRF"). In one embodiment, the transducer 113 is driven to deliver pulsed ultrasound having a carrier frequency of 2 MHz and a PRF of 8 kHz. The DSP 218 provides the appropriate digital commands to the logic circuit 216 to activate a particular mode (i.e., transmit or receive) of operation. The logic circuit 216 generates two digital logic pulse trains V1 and V2 with the specified carrier frequency (divider applied to external clock), PRF, and pulse length. The two pulse trains V1 and V2 signals are provided to an operational amplifier 220 included in the transmit circuit 210, are added 180 degrees out of phase, and amplified by the operational amplifier 220 according to the gain specified by the control signals from the processing system 120.

The operational amplifier 220 is preferred to provide approximately 40 dB of programmable transmit gain. However, amplifiers having other gain characteristics can be used as well. The specified gain is provided to the logic circuit 216 as digital data, which is converted by a digital-to-analog converter ("DAC") 222 into an analog gain signal applied to the operational amplifier 220. The resulting output signal from the operational amplifier 220 is a square "sinusoid" with center voltage of zero volts. The amplified signal is then applied to the transducer 113 through a tuning circuit (not shown in FIG. 3) to drive the transducer 113 to deliver pulsed ultrasound having a pulse period corresponding to the PRF.

With reference to FIG. 3B, the receive circuit 212 receives echo signals detected by the transducer 113. The echo signals are provided to a receive amplifier 224. In one embodiment, the amplifier 224 provides a fixed gain of approximately 40 dB and bandpass filtering with a center frequency of 2 MHz and a bandwidth of approximately 300 kHz. Other carrier frequencies and corresponding center frequencies can be used as well. For each pulse period of delivered ultrasound, the amplified and bandpass-filtered echo signals are sampled at four times the carrier frequency by an analog-to-digital converter ("ADC") 226 to provide digital echo data representative of the amplified and bandpass-filtered echo signals. In the present example, the sampling frequency of 8 MHz based on a carrier frequency of 2 MHz. The echo data are processed by the logic circuit 216 to demodulate the echo signals for a pulse period of ultrasound into Doppler (I,Q) shift samples that stratify the depth range of interest along the ultrasound beam. As known in the art the "I" value represents a measure of a Doppler shift sample along an "in-phase" or "real" axis of the complex plane and the "Q" value represents a measure of the Doppler shift sample at essentially the same time and position, but on a "quadrature" or "imaginary" axis of the complex plane. In addition to the Doppler (I,Q) shift samples, the echo data generated by the ADC 226 are also output by the logic circuit 216. The Doppler (I,Q) shift samples and the echo data generated by the logic circuit 216 are provided to respective DSPs 218 (FIG. 2) to construct Doppler shift signals from multiple Doppler shift samples. Each Doppler shift signal is constructed from Doppler shift samples from the same echo depth and across multiple pulse periods. The Doppler shift signals are represented by Doppler shift data that are output by the respective DSPs 218.

Figure 9:
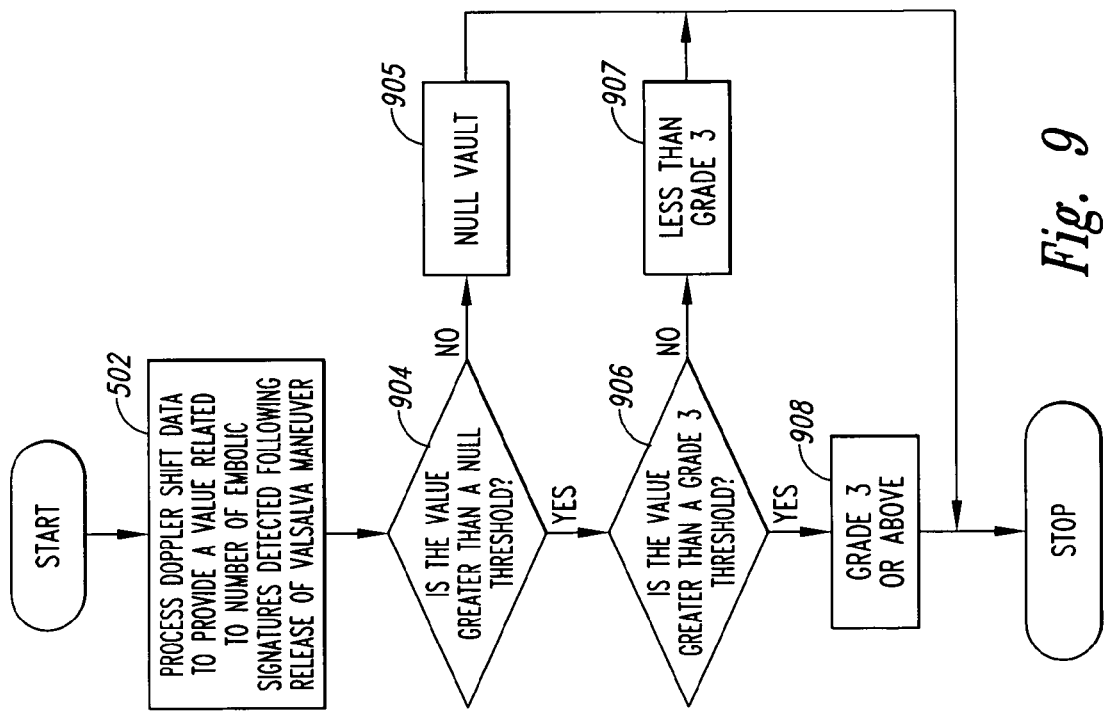
FIG. 9 is a flow diagram for a grading algorithm according to another embodiment of the present invention.

FIG. 9 is a flow diagram illustrating the signal and data processing performed by the DSP platform 200 for echo signals detected by the transducer 113 (FIG. 1). The echo signals are amplified and band-pass filtered at the carrier frequency at step 402. The amplified and band-pass filtered echo signals are then digitized to provide digital echo data representing the amplified and band-pass filtered echo signal at step 404. The echo data is demodulated at step 406 to generate Doppler (I,Q) shift samples for the depth range. The Doppler (I,Q) shift signals are low-pass filtered at step 408 to remove noise outside the bandwidth of the transmit signal. Demodulation and low-pass filtering are performed within each pulse period. At step 410, the low-pass filtered Doppler (I,Q) shift samples are decimated to carry forward only candidate signals from the depth or depth range of interest. Doppler shift signals represented by Doppler shift data are constructed at step 410 from the Doppler (I,Q) shift samples from multiple pulse periods. The Doppler shift signals are clutter filtered at step 412 to suppress "clutter" from each Doppler shift signal. With reference to FIG. 2, steps 402-412 are generally performed by the DSP platform 200.

Suitable methods for demodulating, low-pass filtering and decimating are described in greater detail in the aforementioned U.S. Pat. No. 6,196,972 to Moehring. However, it will be appreciated that other methods can be used as well. In summary, the aforementioned patent describes a demodulation process for generating Doppler (I,Q) shift samples that can be performed through simple subtraction operations operating on each successive quartet of samples of echo data for a pulse period. Each sample corresponds to digital echo data resulting from sampling the signal output by the receive amplifier 224 at four-times the carrier frequency. For a quartet of samples, the third value is subtracted from the first value to produce the real part "I" and the second value is subtracted from the fourth value to produce the imaginary part "Q" of a complex Doppler (I,Q) shift sample for an associated depth. The same operation is performed on all quartets of samples of echo data for a pulse period, with each succeeding quartet of points associated with a location of greater depth. The particular demodulation method blurs the axial resolution by approximately one wavelength of the carrier, but is acceptable in typical applications since one wavelength of the carrier is inconsequential relative to the typical sample volume size associated with medical pulse Doppler ultrasound.

Demodulation into Doppler (I,Q) shift samples is followed by a low-pass filter operation. The low-pass filter operation described in the aforementioned patent involves taking as many as 35 contiguous gate positions bracketing a desired gate depth, within one pulse period, and applying a low-pass finite impulse response ("FIR") filter. The process of low-pass filtering reduces out-of-band noise from a signal which is sampled across successive pulses at a relatively low frequency (i.e., at the PRF). The FIR filter is applied to the Doppler (I,Q) shift samples spanning the depth range bracketing a gate to construct one Doppler (I,Q) shift sample for each particular gate for the particular pulse period.

Clutter cancellation can be accomplished with infinite impulse response ("IIR") filters, as described in detailed in the aforementioned U.S. Pat. No. 6,196,972 to Moehring. However, other clutter cancellation filters can be used as well. The clutter filtered Doppler shift data is then provided to the processing system 120 from the DSP platform 200 where it further processed. For example, the data can be processed by the processing system 120 to construct a PMD image for display on the display 126 (FIG. 1) to provide visual feedback to an operator regarding blood flow in a region interrogated by ultrasound. Although not discussed herein in detail, construction of an image from the Doppler shift data can be accomplished using conventional techniques now known by those ordinarily skilled in the art, for example, as described in the aforementioned U.S. Pat. No. 6,196,972 to Moehring, or later developed. Consequently, in the interest of brevity, a detailed discussion of constructing such an image is omitted from herein.

As previously mentioned, and as will be explained in more detail below, the Doppler shift data provided by the DSP platform 200 can be further processed in order to grade and/or count MESs detected using the ultrasound system 100. The particular embodiment described below is directed to grading functional conductance of PFO according to various grading scales. However, as previously mentioned, alternative embodiments of the present invention can be utilized in other applications as well. From the description provided herein, those ordinarily skilled in the art will obtain sufficient understanding to practice the invention in various applications, and consequently, the scope of the invention should not be limited to the particular embodiments described herein.

Figure 5:
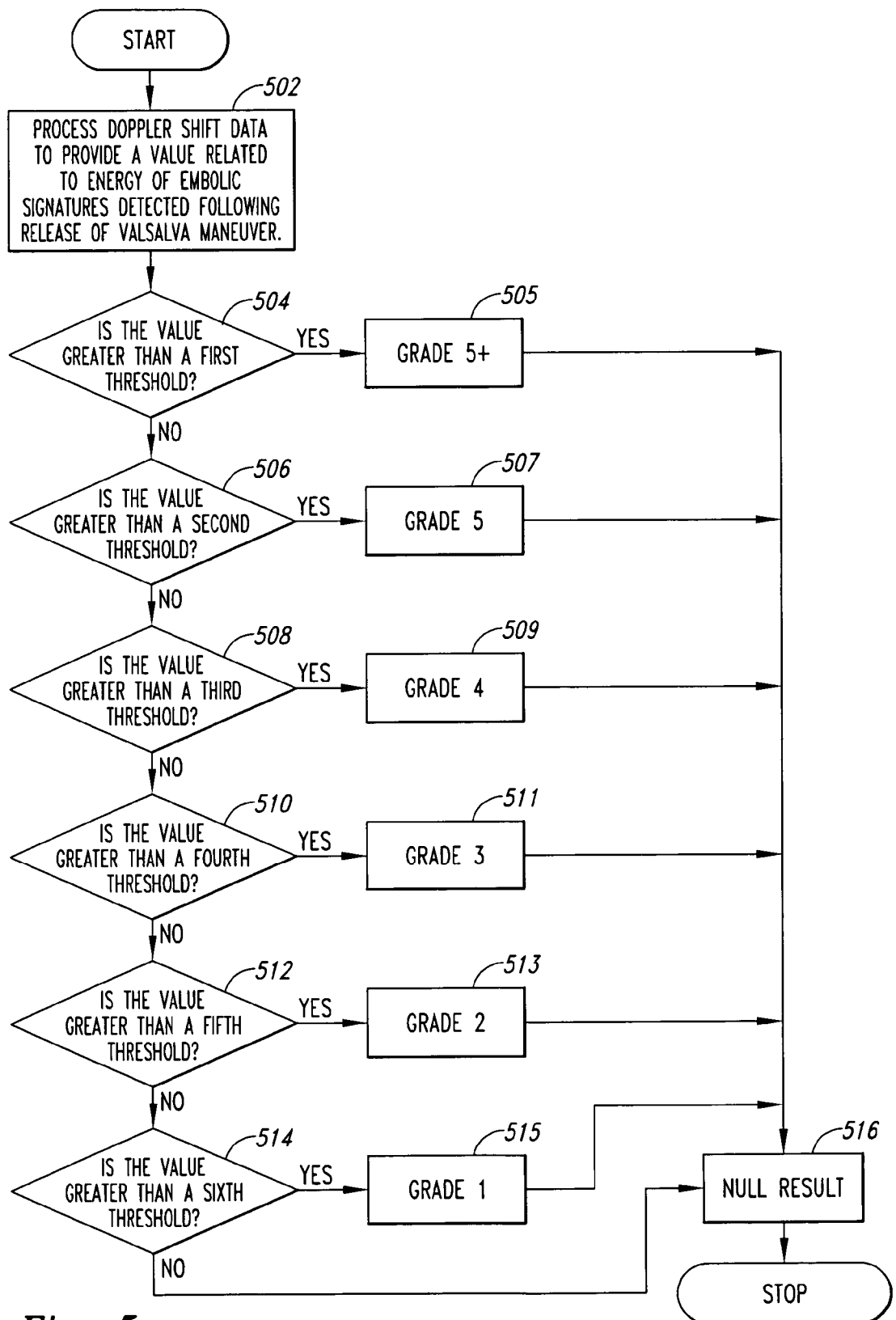
FIG. 5 is a flow diagram for a grading algorithm according to an embodiment of the present invention using Doppler shift data from the DSP platform of FIG. 2.

FIG. 5 is a flowchart for an algorithm that performs automatic grading of the functional conductance of a PFO. The embolic signatures evaluated by the algorithm are bubbles injected into a patient in accordance with a conventional protocol for evaluating PFO in the patient. In one embodiment, the contrast bubble ETs are monitored following the release of the Valsalva maneuver and continues for a time period thereafter. At step 502, the Doppler shift data provided by the DSP platform 200 (FIG. 1) is processed to calculate a value related to the energy of bubble ETs detected following the release of the Valsalva maneuver and during the subsequent monitoring period.

Based on the value calculated, the functional conductance of the PFO is graded according to a grading scale that generally corresponds to a conventional six-level logarithmic scale that is typically used for PFO evaluation based on visually counting bubble ETs detected by a multi-gate pmTCD ultrasound device. The conventional six-level logarithmic grading scale is as follows:

Grade 0=0 ETs,
Grade I=1-10 ETs,
Grade II=11-30 ETs,
Grade III=31-100 ETs,
Grade IV=101-300 ETs, and
Grade V=>300 ETs.

In contrast, the grading scale used in the present embodiment of the invention has seven grades that generally correspond to the conventional grading scale. More specifically, the seven grades are: Grade 0, Grade 1, Grade 2, Grade 3, Grade 4, Grade 5, and Grade 5+ (5+ is distinguished from 5 in that it has at least a two heart cycle period during which there is a homogenous white-out of the spectrum and the m-mode display. The algorithm performs grading at steps 504-516 by comparing the value calculated at step 502 to respective threshold values defining the different grades. The values used for the thresholds will be discussed in more detail below.

In contrast to visually counting the number of bubble ETs, in the present embodiment the energy associated with the bubble emboli is quantified and compared to energy thresholds. Based on the comparison, a grade for the functional conductance of the PFO is made. The grade provided by the algorithm constitutes a finding which informs a physician who will interpret the finding, come to a diagnosis, and determine appropriate clinical management based on the diagnosis. By using the algorithm shown in FIG. 5, having a technician visually count the number of bubble ETs is unnecessary. As a result, the grading performed by the algorithm is less prone to errors, and additionally, can provide a grade much faster than using the conventional method.

Figure 6:
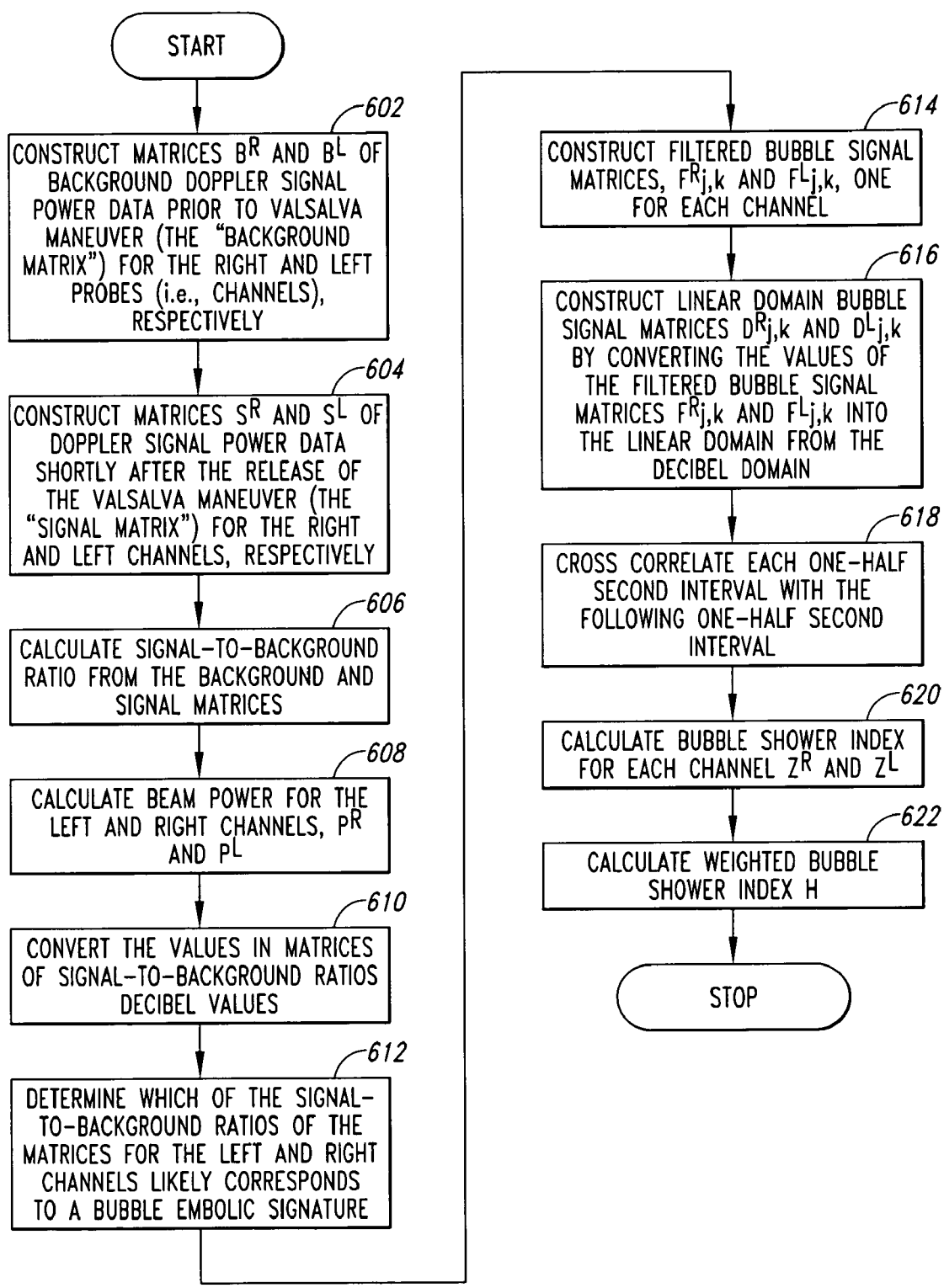
FIG. 6 is a flow diagram for Doppler shift data processing of FIG. 5 according to an embodiment of the present invention.

FIG. 6 is a flowchart that illustrates in greater detail the processing of the Doppler shift data of step 502 (FIG. 5). Matrices will be identified herein by a variable, and entries in a matrix are identified by indices j and k, where j represents a row index and k represents a column index, as known. For example, a matrix Q has a dimension of M rows and N columns. The entries in the matrix Q are identified by $Q_{j,k}$, where j=1 to M and k=1 to N. Additionally, where matrices are constructed for each of the channels, the respective matrix is identified by "R" for the right channel and "l" for the left channel. For example, the matrix Q for the right channel is identified as $Q^R$ and the matrix Q for the right channel is identified as $Q^L$.

At step 602, matrices $B^R$ and $B^L$ of background Doppler signal power data are constructed from Doppler shift data acquired from the left and right channels. In one embodiment, the Doppler signal power is calculated for a period of 10 seconds during normal respiration by the patient, however, time periods other than 10 seconds can be used as well. Assuming that the ultrasound delivered to the patient has a PRF of 8 kHz, and the Doppler shift signal power is calculated using 64 pulse periods (i.e., a Doppler shift signal power value is calculated every 8 ms), 1,250 Doppler shift signal power values are calculated over the 10 seconds of monitoring. Calculating Doppler signal power from the Doppler shift data is known in the art, and consequently, in the interest of brevity, will not be described in detail herein. Using a typical depth range of 44-76 mm, with 2 mm intervals, for monitoring the MCA and ACA results in 17 different depths. Thus, the resulting matrices $B^R$, $B^L$ for the right and left channels, respectively, have dimensions of 17 rows by 1,250 columns.

At step 604, matrices $S^R$ and $S^L$ of signal power data are constructed from Doppler shift data acquired from the left and right channels shortly after the release of the Valsalva maneuver. In one embodiment, the Doppler signal power is calculated for a period of 60 seconds, although in other embodiments different time periods can be used. For 60 seconds of Doppler shift signal power, a matrix of 17 rows by 7,500 columns of Doppler shift signal power is constructed for each channel. The 17 rows represent 17 different depths over the depth range of 44-76 mm in 2 mm gate intervals, and the 7,500 columns represent the number of Doppler shift signal power values calculated over the 60 seconds, each value calculated from 64 pulse periods of ultrasound having a PRF of 8 kHz.

Using the matrices $B^R$, $B^L$, $S^R$ and $S^L$, two signal-to-background ratio matrices $T^R$ and $T^L$ are constructed at step 606. Each of the matrices is constructed by dividing all Doppler shift signal power values $S_{j,k}^R$, $S_{j,k}^L$ in a row of the signal matrix $S^R$, $S^L$ by a mean Doppler Shift signal power ("mean background power vector," $\bar{Z}_j$) calculated from the Doppler shift signal power values $B_{j,k}^R$, $B_{j,k}^L$ in the corresponding row of the corresponding (i.e., left or right channel) background matrix $B^R$, $B^L$. The resulting mean background power vectors $\bar{Z}_j$ define a mean background power matrix for each channel, $Z^R$ and $Z^L$. Each matrix $Z^R$, $Z^L$ has dimensions of 17 rows and 1 column. The 17 rows correspond to the 17 different depths and the 1 column corresponds to a respective mean background power vector at each of the 17 depths.

The two resulting matrices (i.e., left and right channels) of signal-to-background ratios $T^R$, $T^L$ have dimensions of 17 rows by 7,500 columns. Although in the present embodiment a mean background power value is calculated, a median power value can be alternatively used in calculating the values $T_{j,k}^R$, $T_{j,k}^L$ for the matrices of signal-to-background ratios $T^R$, $T^L$.

$$T_{j,k} = \frac{S_{j,k}}{\bar{B}_j} \qquad (0.1)$$

$$\text{where, } \bar{B}_j = \frac{\sum_{k=1}^{N_b=1250} B_{j,k}}{N_b}$$

At step 608, a beam power analysis is performed for each channel. Using the median background power vectors $Z_j$ in the matrices $Z^R$ and $Z^L$, the vectors are summed from each channel to provide to values $P^R$ and $P^L$ corresponding to the beam power for each of the channels. The values $P^R$ and $P^L$ are expressed in terms of decibels.

$$P = 10 \log_{10}\left(\sum_{j=1}^{M} Z_j\right) \qquad (0.2)$$

$$\text{Where, } Z_j = \underset{k}{median}(B_{j,k})$$

At step 610, the signal-to-background ratios $T_{j,k}^R$, $T_{j,k}^L$ of the matrices $T^R$, $T^L$ are converted into decibels, and result in two matrices $V^R$ and $V^L$.

$$V_{j,k} = 10 \log_{10} T_{j,k} \qquad (0.3)$$

At step 612, the matrices $V^R$ and $V^L$ are analyzed to determine which of the signal-to-background ratios (in dB) likely correspond to a bubble embolic signature. In the present embodiment, every signal-to-background ratio $V_{j,k}^R$, $V_{j,k}^L$ of the matrices $V^R$ and $V^L$ exceeding a factor of 10 is considered to be a likely candidate corresponding to a bubble signal. The results of the determination are used to construct two binary bubble signal matrices $\beta^R$ and $\beta^L$ (i.e., one for the right channel and one for the left channel). Each binary matrix $\beta^R$, $\beta^L$ includes binary values $\beta_{j,k}^R$, $\beta_{j,k}^L$ ("1" or "0") arranged in 17 rows and 7,500 columns. Each "1" indicates that the signal-to-background ratio $V_{j,k}^R$, $V_{j,k}^L$ for the corresponding location in the matrix of signal-to-background ratios $V^R$, $V^L$ exceeded a factor of 10 and each "0" indicates that the signal-to-background ratio $V_{j,k}^R$, $V_{j,k}^L$ for the corresponding location in the matrix of signal-to-background ratios $V^R$, $V^L$ did not exceed a factor of 10. At step 614, filtered bubble signal matrices $F^R$ and $F^L$ are constructed for each channel by multiplying the signal matrices $V^R$ and $V^L$ (in dB) with the binary matrices $\beta^R$, $\beta^L$.

$$F_{j,k} = (\beta_{j,k})(V_{j,k}) \qquad (0.4)$$

where $$\beta_{j,k} = \begin{cases} 1, & \text{if } V_{j,k} \geq 10 \text{ dB} \\ 0, & \text{if } V_{j,k} < 10 \text{ dB} \end{cases}$$

Each of the matrices $F^R$ and $F^L$ have dimensions of 17 rows by 7,500 columns. At step 616, linear domain bubble matrices $D^R$ and $D^L$ are constructed for each channel by converting the values $F_{j,k}^R$, $F_{j,k}^L$ of the filtered bubble signal matrices $F^R$ and $F^L$ into the linear domain from the decibel domain.

$$D_{j,k} = 10^{F_{j,k}/10} \qquad (0.5)$$

At step 618, cross correlation of each one-half second interval with the following one-half second interval is performed. Although the "magnitude" or severity of the bubble embolic signatures could be determine by summing the energy of the isolated bubble signals from the linear domain bubbles matrices $D^R$ and $D^L$, the backscatter from bubbles which have a size distribution much smaller than a millimeter will fall into the Raleigh scattering region for 2 MHz ultrasound ($\lambda$=780$\beta$). As known, in this scattering region the acoustic backscatter will vary as the 6th power of the diameter of the bubbles. As a result, there can be significant variation in bubble backscatter represented by the signals (and the addition of these signals) of the matrices $D^R$ and $D^L$. Consequently, an approach that extracts a shower description parameter from the matrices $D^R$, $D^L$ based on a cross correlation is utilized.

Each of the matrices $D^R$ and $D^L$ are divided into sets of overlapping sub-matrices having dimensions of 17 rows and 128 columns. Each of the sub-matrices roughly represents data for 17 different depths over approximately a one second period. In the present embodiment, the overlap between adjacent sub-matrices is 50%. A matrix A(i) is defined having the first 64 columns in a given sub-matrix (dimensions M=17 rows by $N_m$=64 columns), where i denotes the index of the sub-matrix. As a result, there are 116=int($N_s/N_m$)-1 sub-matrices in 60 seconds of data. Similarly, matrix B(i) is defined having the last 64 columns of the same sub-matrix, where i denotes the particular sub-matrix. The algorithm calculates and integrates a correlative vector, $R_i$, for each of the sub-matrices, and thereby formulate a vector $C^R$, $C^L$ for each channel as follows (C has dimensions 1×116):

$$C_i = \sum_{l=1}^{int(N_s/N_m)-1} R_i(l) \qquad (0.6)$$

-continued $$\text{where, } R_i(l) = \sum_{j=1}^{M} \sum_{k=0}^{N_m-1} A(i)_{j,k} B(i)_{j,[(k+l) \% N]}$$

$C^R$, $C^L$ are referred to as "bubble vectors" because they are primary indicators of when bubble shower activity is occurring across the 60 seconds following bubble injection for PFO detection. The amplitude of the individual bubbles towards the magnitude of $C^R$, $C^L$ is somewhat softened compared to the amplitude contributions towards directly summing the signals in matrices $D^R$, $D^L$. Bubbles that do not have neighboring bubbles do not make as strong a contribution as bubbles with nearby neighbors.

At step 620, a shower index is calculated. The $C^R$, $C^L$ vectors are summed and converted to decibels to give two floating point values $Z^R$ and $Z^L$ corresponding to the bubble values in the two channels.

$$Z_j = 10 \log_{10}\left(\sum_j C_j\right) \qquad (0.7)$$

The particular autocorrelation measure increases with the intensity of bubble showers and with duration of bubble showers. The operation results in a parameter for sorting high grade showers from low grade showers. At step 622, the shower indices $Z^R$ and $Z^L$ are weighted according to their beam values to produce a weighted shower index H.

$$H = \begin{cases} \dfrac{(2fZ_L) + Z_R}{2f + 1} & \text{if } P^L > P^R \\ \dfrac{(2fZ_R) + Z_L}{2f + 1} & \text{if } P^R > P^L \end{cases} \qquad (0.8)$$

Where, $$f = \frac{\text{abs}(P^L - P^R)}{3}$$

The weighted shower index H is the value that is used for grading the functional conductance of the PFO. In one embodiment, a seven-level grading scale is used for the functional conductance of the PFO.

$$G \begin{cases} 0, & \text{if } H < 40 \text{ dB} \\ 1, & \text{if } H \geq 40 \ \& \ H < 60 \text{ dB} \\ 2, & \text{if } H \geq 60 \ \& \ H < 80 \text{ dB} \\ 3, & \text{if } H \geq 80 \ \& \ H < 100 \text{ dB} \\ 4, & \text{if } H \geq 100 \ \& \ H < 110 \text{ dB} \\ 5, & \text{if } H \geq 110 \ \& \ H < 125 \text{ dB} \\ 5+, & \text{if } H \geq 125 \end{cases} \qquad (0.9)$$

With reference to FIG. 5, the first threshold from step 504 is 125 dB, the second threshold from step 506 is 110 dB, the third threshold from step 508 is 100 dB, the fourth threshold from step 510 is 80 dB, the fifth threshold from step 512 is 60 dB, and the sixth threshold from step 514 is 40 dB. Other embodiments of the invention can use different threshold values. The threshold values have been provided herein by way of example. Alternative embodiments of the present invention can use different threshold values, and additionally, other alternative embodiments can use greater or fewer grade levels than that previously described.

Figure 7A:
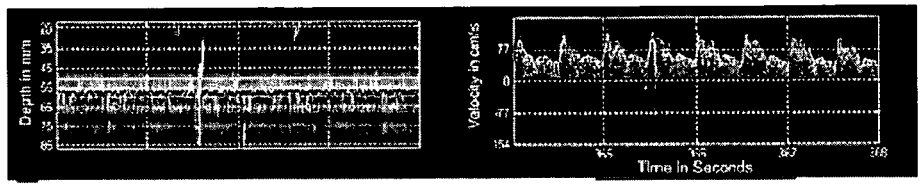
FIGS. 7A-7F are PMD/spectrogram images for various grades of functional conductance of PFO.
Figure 7B:
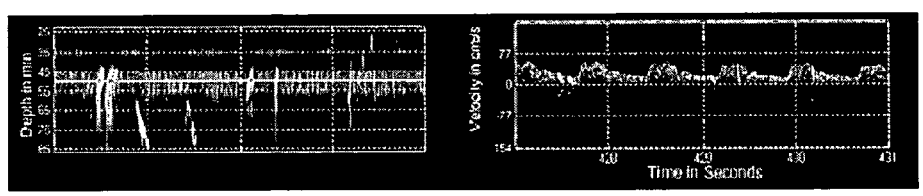
Figure 7C:
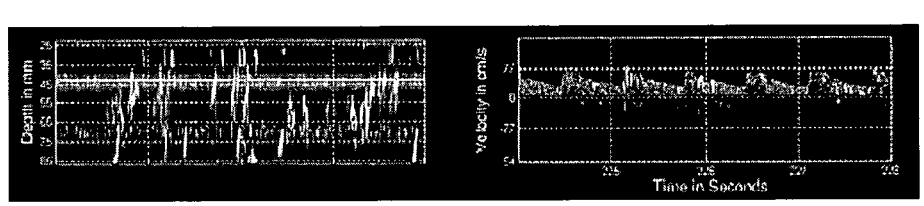
Figure 7D:
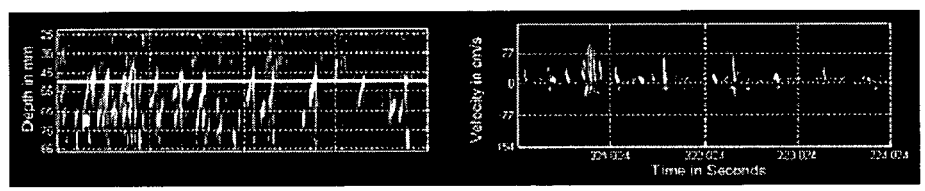
Figure 7E:
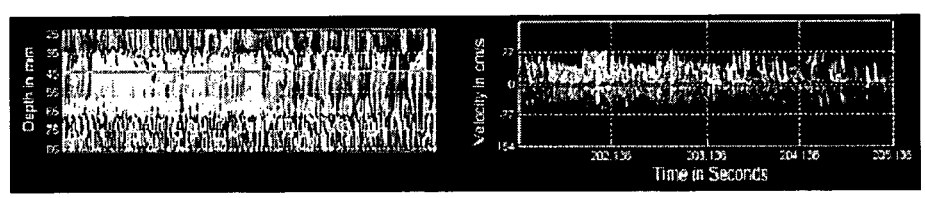
Figure 7F:
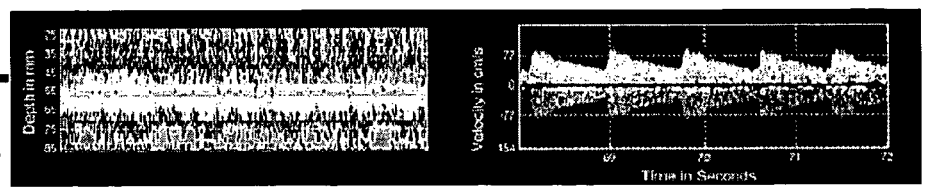

FIGS. 7A-7F are a series of PMD/spectrogram images for different patients of a study that included 200 patients for which data was gathered. There was some overlap with the patient population noted in Spencer et al., Power M-Mode Transcranial Doppler for Diagnosis of Patent Foramen Ovale and Assessing Transcatheter Closure, *J Neuroimaging* 2004; 14:342-349. The PMD/spectrogram images of FIGS. 7A-7F are taken over a four second period following the release of the Valsalva maneuver. The images correspond to the different shower grades of the seven-level grading scale, as previously mentioned, where grades are assigned as follows: grade 0=no emboli ("null hypothesis" is not shown in Figure), grade 1=1-10 emboli (FIG. 7A), grade 2=11-30 emboli (FIG. 7B), grade 3=31-100 emboli (FIG. 7C), grade 4=101-300 emboli (FIG. 7D), grade 5=in excess of 300 emboli (FIG. 7E), and grade 5+="white out" for at least two cardiac cycles (FIG. 7F). Although FIGS. 7A-7F illustrate four second periods, the grading, as previously discussed, is based on the number of embolus visually counted over a 60 second period of monitoring. As illustrated in FIGS. 7A-7C, individual ETs, which appear in the images as vertical streaks in both the PMD and spectrogram images, are easily appreciated for grades 1, 2 and 3. The emboli that make it across the shunt are generally distributed across time sufficiently to allow for individual discrimination. However, counting individual emboli becomes more problematic when considering grades 4, 5 and 5+. As can be seen in FIGS. 7D-7F, the ETs for these higher grades begin to blend together in a way that is explained by the presence of multiple emboli in proximity to the ultrasound beam at any given time. Counting emboli in this context is difficult given the axial resolution limitation of the ultrasound beam as well as the limited patience of the ultrasound technologist, and therefore a different way to grade these larger "uncountable" showers is desirable. When emboli are countable, on the other hand, as in the lower Spencer grades (1-3), then detecting them individually is feasible with a machine algorithm. The analysis described below was performed retrospectively on data acquired from 200 patients undergoing PFO diagnostic examination with PMD. The analysis was comprised of "training" an algorithm in a set of 100 patients and then re-evaluating its performance in a second set of 100 patients.

Instrumentation. A TCD 100M digital 2-MHz Doppler platform (Spencer Technologies, Seattle, Wash.) was used in all exams. The TCD 100M platform has 33 gates placed at 2 mm intervals along the ultrasound beam. The M-mode display covers a depth range of 25-85 mm and there is an accompanying spectrogram which presents spectral analysis of a user-selected depth in the M-mode display. The insonation method for this equipment has been described in Moehring et al., Power M-Mode Doppler (PMD) For Observing Cerebral Blood Flow and Tracking Emboli, *Ultrasound in Med. & Biol.*, Vol. 28, No. 1, pp. 49-57, 2002. The ultrasound beam can observe the proximal MCA and the proximal ACA concurrently in most patients. Bilateral monitoring was performed with each probe held in place over a temporal bone by a Marc 600 head frame (Spencer Technologies, Seattle, Wash.). An MCA gate was selected for each spectrogram. A computer hard disk provided continuous recording that was replayed for manual counting bubble embolic signals, and then used in training the automatic grading algorithm.

Embolic Criteria. The standard for MESs on the sgTCD has been previously defined by an international consensus group in Ringelstein et al., Consensus On Microembolus Detection By TCD, *Stroke* 1998; 29:725-729. However, as previously mentioned, pmTCD produces unique signatures of emboli, appearing as brightly colored ETs as they pass through the insonated arteries. These tracks are more fully described in the Moehring et al. article, and additionally, U.S. Pat. Nos. 6,547,736 to Moehring et al., which is incorporated herein by reference. As described therein, when an embolus moves toward the transducer, a bright red upward-sloping ET is produced. In contrast, when an embolus moves away from the transducer, a bright blue downward-sloping ET is produced. The sloping feature of the ET is prima facie evidence of an embolus (i.e. a bubble or particle) carried by the blood through a vessel within the ultrasound beam. The slope shows the embolus velocity as a change in depth over time. If the single gate is placed in any of the colored bands, ETs also appear on the spectrogram as spectral MESs. In the study, the ETs in the bilaterally insonated arteries from a depth of 46 mm to 76 mm were used for grading—both automatic and manual—since there is a beam overlap with the beam from the opposite side of the head at the midline (i.e., a depth of 75 mm).

Patient population. A single-group, descriptive study was conducted to evaluate the accuracy of the automated grading algorithm for diagnosing PFO. Non-probability consecutive sampling technique was used to enroll 200 patients referred to the Spencer Vascular clinic from June 2003 to November 2003. These patients were referred due to re-current ischemic stroke (n=75, 37.5%) or transient ischemic attack related to presumed paradoxical embolism (n=18, 9%) or active recurrent migraine (n=71, 35.5%) or stroke like symptoms (n=54, 27%), Divers (n=4, 2%). All 200 patients underwent a pmTCD examination evaluation of PFO prior to the analysis presented herein. Patients were precluded from this study if the probe position changed or patient was talking or snoring or there were bruits or high velocity jets in the gathered data during the course of their pmTCD examination evaluation. The sample ranged in age from 16 to 86 years with a mean of 55 years and a male to female ratio of 0.37:0.63. All examinations were performed in response to referrals by attending physicians, and all patients signed informed consent to use their data in scientific publications. Bilateral temporal bone ultrasound windows were identified in all patients except for 3 females (1.5%) and 1 male (0.5%) who were 81, 49, 77 and 78 years of age. In these four patients, unilateral TCD monitoring was performed and the embolic assessments were essentially multiplied by two to obtain bilateral results.

Testing procedure. The Spencer PFO protocol was followed for all the patients in the study, which is a superset of the patients studied in the Spencer et al. article. A minimum of 2 contrast bolus injections were agitated and administered antecubitally (arm vein) while the patient was in recumbent position. The first injection was performed during normal respiration and the second performed immediately prior to a calibrated Valsalva. As suggested in Spencer et al. article, the best results are obtained when a Valsalva is performed during bubble injection. Only the data associated with Valsalva was used in developing the automatic grading algorithm according to the previously described embodiment. However, those ordinarily skilled in the art will appreciate that in procedures such as open heart surgery, the Valsalva is irrelevant to detecting and grading embolic showers, and therefore, embodiments of the present invention are not limited to obtaining data from a protocol that includes a Valsalva maneuver.

Manual Grading Procedure. The conventional RLS conductance grading system has been described in detail in the Spencer et al. article, as well as described herein. The conventional six-level logarithmic scale previously described was used to grade RLS conductance for both the resting and Valsalva injections. Specifically: grade 0=0 ETs, grade I=1-10 ETs, grade II=11-30 ETs, grade III=31-100 ET grade IV=101-300 ETs, and grade V>300 ETs.

Automated grading procedure. As previously discussed, a modified version of the Spencer RLS conductance grading system was used. More specifically, instead of a six-level grading system of 0-5, a seven-level grading system of 0-5+ was used. As in the conventional RLS conductance grading system, only the ETs in the bilaterally insonated arteries from a depth of 46 mm to 76 mm were used for grading since there is a beam overlap at the midline at a depth of 75 mm. As previously described, the Valsalva data is initially normalized using a background signal collected prior to the Valsalva injection. This allows isolation of the ETs from the background blood flow. A numerical method is then used to quantify the ET power intensities.

Assumptions regarding protocol. The following assumptions are made for the protocol in acquiring the data:

1. STATIONARY PROBE. The probe is positioned with a blood flow signal in view, and the probe position does not change over the entire exam. Signals which indicate probe motions are excluded from grading analysis.

2. NORMAL FLOW. Signals which indicate bruits (e.g., vessel wall vibrations due to pathology such as stenosis or spasm) or high velocity jets in the gathered data, which by their nature will confound power assessments associated with bubble injections, are excluded from grading analysis.

3. No SNORING/TALKING. Signals indicative of talking or snoring during the course of the exam are excluded from grading analysis.

Separation of significant PFO (G>=4) from PFO of lesser conductance grades (G<4) was performed by automatic grading and compared to technologist performance for the training group of 100 subjects. Against the conventional process of having a technologist manually count the bubble ETs, the automatic grading algorithm had 94% sensitivity, 92% specificity, 8% false positive rate and 6% false negative rate (p<0.0001) for the training group. Similarly, detection of conductance grade range G>=4 was performed in the test group with 96% sensitivity, 96% specificity, 4% false positive rate and 4% false negative rate (p<0.0001).

Figure 8:
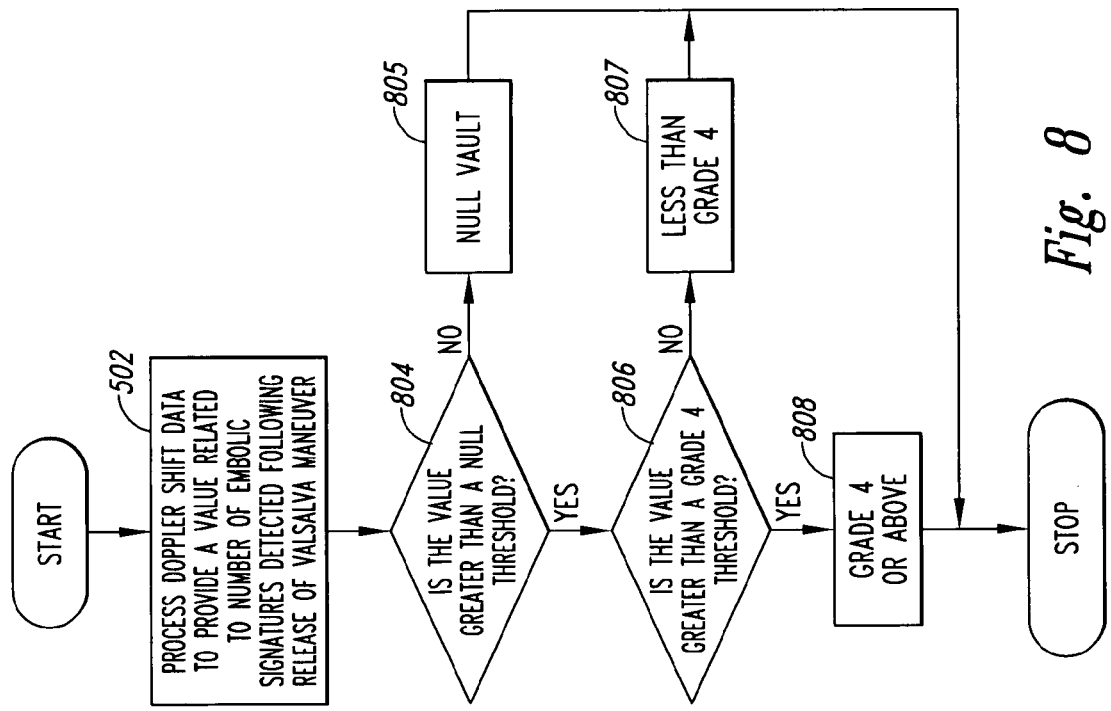
FIG. 8 is a flow diagram for a grading algorithm according to another embodiment of the present invention.

The results of the analysis suggests another embodiment of the present invention, where the algorithm for automatic grading of the functional conductance of a PFO, described with reference to FIG. 5, is modified from the seven-level grading scale to a simplified three-level grading scale, as shown in FIG. 8. In contrast to the automatic grading of FIG. 5, the grading algorithm of FIG. 8 uses the value calculated from the Doppler shift data processing of FIG. 6 to determine whether there is a null result (steps 804 and 805), a grade lower than grade 4 (steps 806 and 807), or a grade of grade 4 or higher (steps 806 and 808). As with the information provided by the automatic grading algorithm of FIG. 5, the information provided by the automatic grading algorithm of FIG. 8 constitutes a finding which informs a physician who will interpret the finding, come to a diagnosis, and determine appropriate clinical management based on the diagnosis.

FIG. 9 illustrates a grading algorithm according to another embodiment of the present invention. As with the grading algorithm shown in FIG. 8, the algorithm of FIG. 9 uses a simplified three-level grading scale. However, in contrasts to FIG. 8, the grading algorithm of FIG. 9 uses the value calculated from the Doppler shift data processing of FIG. 6 to determine whether there is a null result (steps 904 and 905), a grade lower than grade 3 (steps 906 and 907), or a grade of grade 3 or higher (steps 906 and 908). As illustrated by the automatic grading algorithms of FIGS. 5, 8, and 9, the value calculated by the Doppler shift data processing can be used in grading scales having different grade levels.

The previously discussed embodiments of algorithms for automatic grading of embolic signatures, which were directed to grading the functional conductance of a PFO, used a value that quantified the energy associated with the bubble emboli and is compared to energy thresholds in determining a grade. In alternative embodiments of the present invention, quantifying the energy associated with embolic signatures can be combined with an algorithm that identifies and "counts" ETs. As with the previously described embodiments, the present embodiment will be described with respect to the specific application of grading the functional conductance of a PFO.

Figure 10:
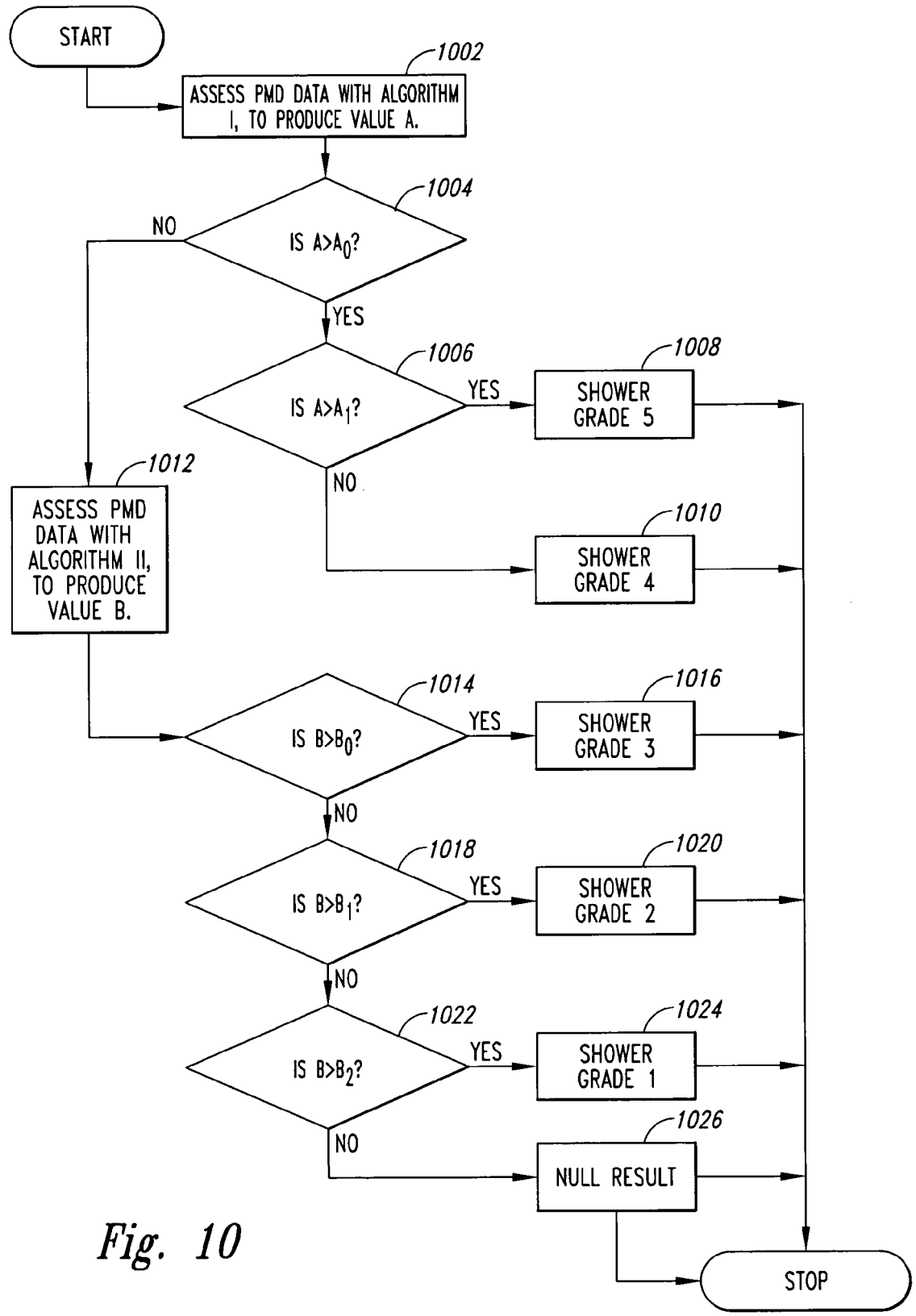
FIG. 10 is a flow diagram for a grading algorithm according to another embodiment of the present invention.

FIG. 10 is a flow chart of a grading/counting algorithm according to an embodiment of the invention for MESs that are monitored using a multi-gate Doppler ultrasound system. The algorithm shown in FIG. 10 uses a six-level grading scale, with grades 0-5. As will be described in more detail below, the algorithm combines quantification of the energy associated with the bubble emboli and automatic identification and counting of ETs.

At step 1002, the Doppler shift data is processed to calculate a first value related to the bubble ETs that are detected following the release of the Valsalva maneuver and during the subsequent time period of monitoring. In the present embodiment, the first value represents the energy associated with the bubble emboli. The process described with reference to FIG. 6 can be used to calculate the first value. At step 1004, the first value is compared to a first threshold value. In the present embodiment, the first threshold value corresponds to the energy threshold for a grade 4 according to the modified seven-level grading scale previously discussed, that is, 100 dB. If the first value is greater than 100 dB, another comparison is made at step 1006 to the energy threshold for grade 5, which has been previously described as being 110 dB. A grade 5 is reported at step 1008 in the event the first value from step 1002 is greater than 110 dB, and a grade 4 is reported at step 1010 otherwise.

At step 1004, if the first value calculated at step 1002 is less than 100 dB, the Doppler shift data collected from monitoring the bubble emboli following the release of the Valsalva maneuver is further processed at step 1012 to provide a second value. The second value generally corresponds to the number of ETs that are identified as bubbles over a time period of analysis. In one embodiment, the second value is compared at step 1014 to a threshold value that corresponds to the grade 3 threshold of the conventional six-level Spencer RLS conductance grading scale, in particular, 31 ETs. A grade 3 is reported at step 1014 if the second value is greater than 31. However, in the event the second value is not greater than 31, the second value is compared to a threshold value corresponding to the grade 2 threshold at step 1018, that is, 11 ETs, and is reported as a grade 2 at step 1020 if the number of bubble ETs detected is greater than 11. At steps 1022, 1024, and 1026, if the second value is not greater than 11, then a grade of 1 or a null result is reported at steps 1024 and 1026, respectively, depending on the comparison of the second value at step 1022 to a threshold value that corresponds to a grade 1 threshold, namely, 1 ET. The grade provided by the automatic grading/counting algorithm of FIG. 10 constitutes a finding which informs a physician who will interpret the finding, come to a diagnosis, and determine appropriate clinical management based on the diagnosis.

The particular embodiment of the automatic grading/counting algorithm illustrated in FIG. 10 uses an energy value for the bubble ETs in making a determination between reporting a grade 5 or grade 4. For grades less than grade 4, however, the number of bubble ETs detected over the period of evaluation is used to make the grade. The particular details of the automatic grading/counting algorithm of FIG. 10 can be modified to provide alternative embodiments. For example, the energy value provided by step 1002 can be used to make a determination between grades higher than a grade 3, and the count value provided by the processing of step 1012 can be used to make a determination for grades lower than grade 3. In another embodiment, not all of the grades between 0 and 5, or 5+, need to be represented. That is, the energy value can be used to determine only if the grade is higher than a grade 4, and if not, identification of a specific grade of 3 or lower can be made using the count value from step 1012. Such modifications are well within the knowledge of those ordinarily skilled in the art, and consequently, will obtain sufficient understanding to practice the various embodiments of the invention from the description provided herein.

Figure 11:
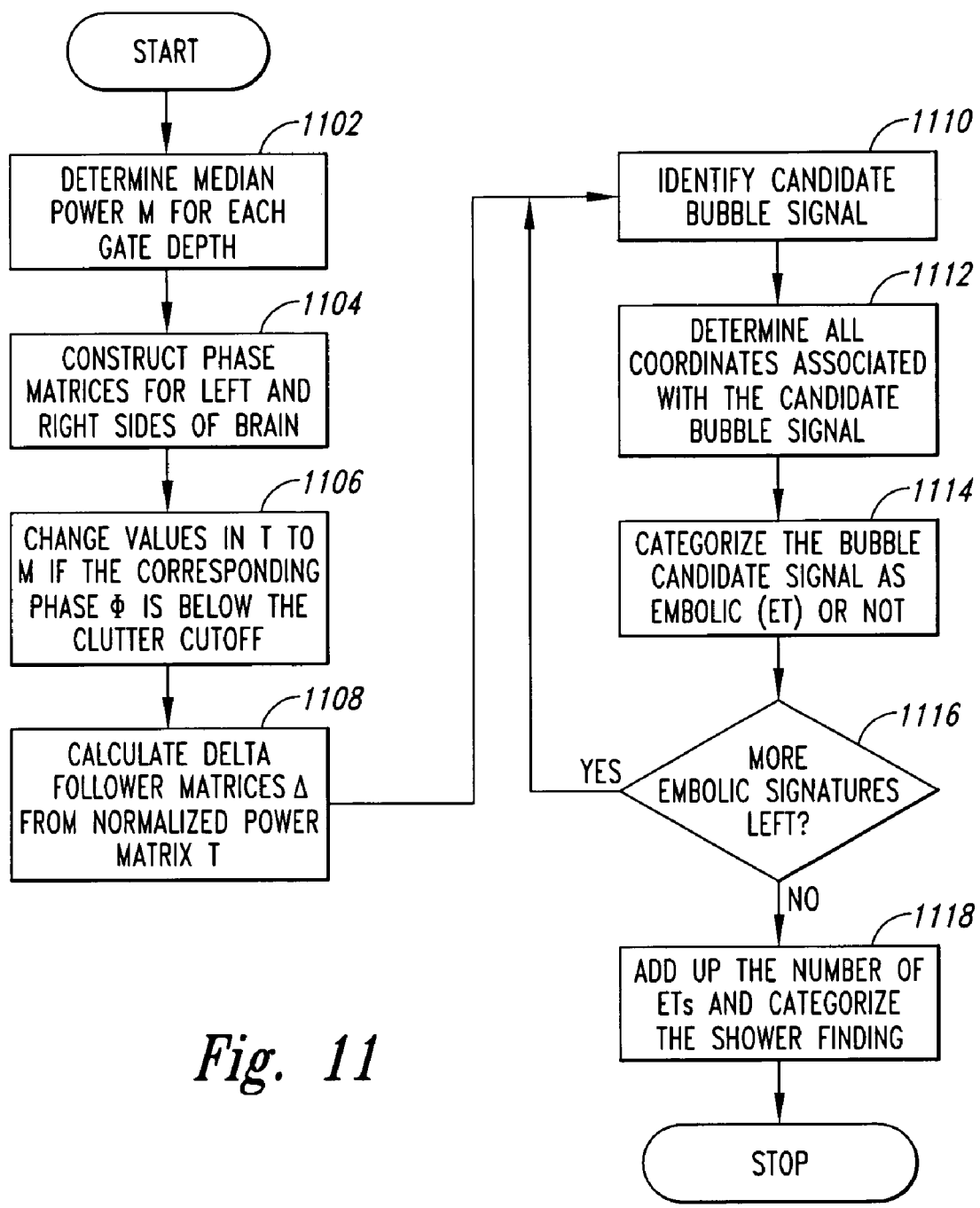
FIG. 11 is a flow diagram for Doppler shift data processing of FIG. 10 according to an embodiment of the present invention.

FIG. 11 is a flowchart for Doppler shift data processing at step 1012 (FIG. 10) according to an embodiment of the present invention. The Doppler shift data is further processed to take advantage of the fact that the bubble embolic showers have "countable" ETs, and can be used to produce a count from which the PFO grade for a grade lower than grade 4 can be directly determined. At step 1102, the $T^R$ and $T^L$ matrices of signal-to-background ratios $T_{j,k}^R$, $T_{j,k}^L$ constructed at step 1002 (FIG. 10) are processed to construct median power matrices $M^R$, $M^L$. For each of the 17 rows of signal-to-background ratios $T_{j,k}^R$, $T_{j,k}^L$ a median power value is calculated and represents an entry $M_j^R$, $M_j^L$ in the median power matrices $M^R$, $M^L$. Each of the $M^R$, $M^L$ matrices have a dimension of 17 rows and 1 column.

$$M_j = \underset{k}{median}(T_{j,k}) \tag{0.10}$$

At step 1104, the Doppler shift data is processed to construct phase matrices $\phi^R$, $\phi^L$ having phase entries $\phi_{j,k}^R$, $\phi_{j,k}^L$. The phase matrices $\phi^R$, $\phi^L$ are representative of the mean blood flow velocity calculated from the clutter filtered Doppler shift data for the 17 different depths and over the 60 seconds of monitoring. In the present embodiment, each phase value $\phi_{j,k}^R$, $\phi_{j,k}^R$ is calculated from the data for one depth and across 64 pulse-periods. As a result, the phase matrices $\phi^R$, $\phi^L$ have dimensions of 17 rows by 7,500 columns. Conventional methods can be used to calculate the phase values $\phi_{j,k}^R$, $\phi_{j,k}^L$. An example of the Doppler shift data processing is described in more detail in aforementioned U.S. Pat. No. 6,196,972 to Moehring.

At step 1106, a phase-based correction to the power values is performed. The power value for any data point with a phase less than $$\frac{\pi}{40}$$

(approximately 7 cm/s) is replaced with the median power value $M_j^R$, $M_j^L$ for that gate depth. The correction in essence fills in a median power value where the background has been filtered away with clutter cancellation filtering. The expression for the phase correction is:

$$\text{if } \phi_{j,k} < \frac{\pi}{40} \tag{0.11}$$
$$\text{then } T_{j,k} = M_j$$

At step 1108, a delta follower matrices $\Delta^R$, $\Delta^L$ are constructed. That is, a trace aimed at following the background power is calculated. The construction of the delta follower array is for eliminating background blood flow signals so that the remaining signals are ETs that are amenable to counting. Conventional methods known to those ordinarily skilled in the art can be used in constructing the delta follower arrays, including the process described in U.S. Pat. No. 6,547,736 to Moehring et al. The "delta" refers to changes in signal power due to the presence of an embolus. The delta follower arrays are constructed according to the following rules, which are applied by looping through all values of k for each row j:

$$\delta_{j,k} = \delta_{j,k-1} \tag{0.12}$$
$$\text{if } \phi_{j,k} > \frac{\pi}{20}$$
$$\text{then } \delta_{j,k} = \begin{cases} \delta_{j,k-1} + 0.5 & \text{if } T_{j,k} > \delta_{j,k-1} \\ \delta_{j,k-1} - 0.5 & \text{if } T_{j,k} < \delta_{j,k-1} \end{cases}$$

The delta array values $\Delta_{j,k}$ are constructed by determining the absolute difference between the assigned delta values $\delta_{j,k}$ and the power values $T_{j,k}$ at the current location. The step essentially subtracts off background signal (which can be a blood flow signal) from embolic signals:

$$\Delta_{j,k} = |\delta_{j,k-1} - T_{j,k}| \tag{0.13}$$

At steps 1110-1118, the bubble ETs are detected for counting and grading. The delta array values $\Delta_{j,k}$ are tested against a preset threshold to identify a candidate bubble signal $B_{j,k}$ at spatial index i and time index j. Once a bubble value is identified, its location and its signal power are stored. The neighboring pixels are interrogated using the same steps to determine the bubble's boundaries. When a candidate bubble is thus isolated, it is subjected to a set of inclusion criteria to be counted as an ET. The inclusion criteria are based on a priori information about emboli. For example, for a candidate bubble signal to be counted as a bubble ET, it must have a sloping presentation—a change in depth with a change in time—to indicate motion through the vasculature. The following three steps are performed inside a loop which searches the $\Delta$ matrices ($\Delta^L$ and $\Delta^R$) for embolic signals.

At step 1110 a preliminary test is done to see if the delta matrix value $\Delta_{j,k}$ exceeds 10 dB for any coordinate pair (j,k). The first such location discovered is taken to be a candidate bubble signal $B_{j,k}$. Steps 1112 and 1114 are performed on the candidate bubble signal $B_{j,k}$ and step 1110 is repeated to find the next candidate bubble signal.

if $\Delta_{j,k} > 10$ then $B_{j,k} = \Delta_{j,k}$ (0.14)

else no bubble candidate at location j,k

At step 1112, once a candidate bubble signal $B_{j,k}$ is identified, its j,k coordinates are stored in a candidate bubble list $L_i = \{j,k\}$. The set of samples that constitute this candidate bubble signal are then determined by looking for all contiguous samples such that $\Delta_{j',k'} > 10$. The list of values (j',k') for which $\Delta_{j',k'} > 10$, which includes (j, k) and for which there is an accompanying list of Δ values, constitutes the candidate bubble list $L_i$. In the present example, construction of the candidate bubble list $L_i$ is accomplished by using 2-D recursive exploration of matrix sahples in the vicinity of (j,k) until values for which Δ>10 are exhausted. However, other methods of constructing the candidate bubble list $L_i$ can be used as well. Once the candidate bubble list $L_i$ and associated power values are extracted, all these locations in the source matrix Δ are set to a background power value to guarantee that they are not rediscovered through a subsequent recursive search when finding the "next" candidate signal in step 1110.

At step 1114, after the candidate bubble list $L_i$ is constructed for the candidate bubble signal $B_{j,k}$, the candidate bubble signal $B_{j,k}$ is confirmed or rejected as a bubble ET based on the following criteria:

(1) Size: the total number of coordinate pairs in the candidate bubble list $L_i$ must be between 10 and 200.

(2) Slope: a linear regression is performed on the coordinate pairs in the candidate bubble list $L_i$ to calculate the slope. The calculated slope is expected to be greater than 70 but less than 2000 (these are unit-less ratios of indices) to be considered a bubble.

The previously described criteria for confirming or rejecting a candidate bubble signal $B_{j,k}$ as a bubble ET has been provided by way of example. Other rules or criteria can be used as well. For example, a simplistic surrogate for the slope requirement might be requiring that the coordinate set span a fixed number of rows and columns. More generally, the specific example provided herein is intended to demonstrate that a priori information about emboli of interest moving in blood flow for a given application or vessel can be used in a grading/counting algorithm at these steps in the algorithm to maximize specificity for the embolic phenomena of interest.

At step 1118, once all the bubbles ETs are identified, the bubble ETs are summed for both channels. The grade is then determined as 0, 1, 2 or 3 according to the conventional six-level manual grading scale previously discussed.

Figure 12:
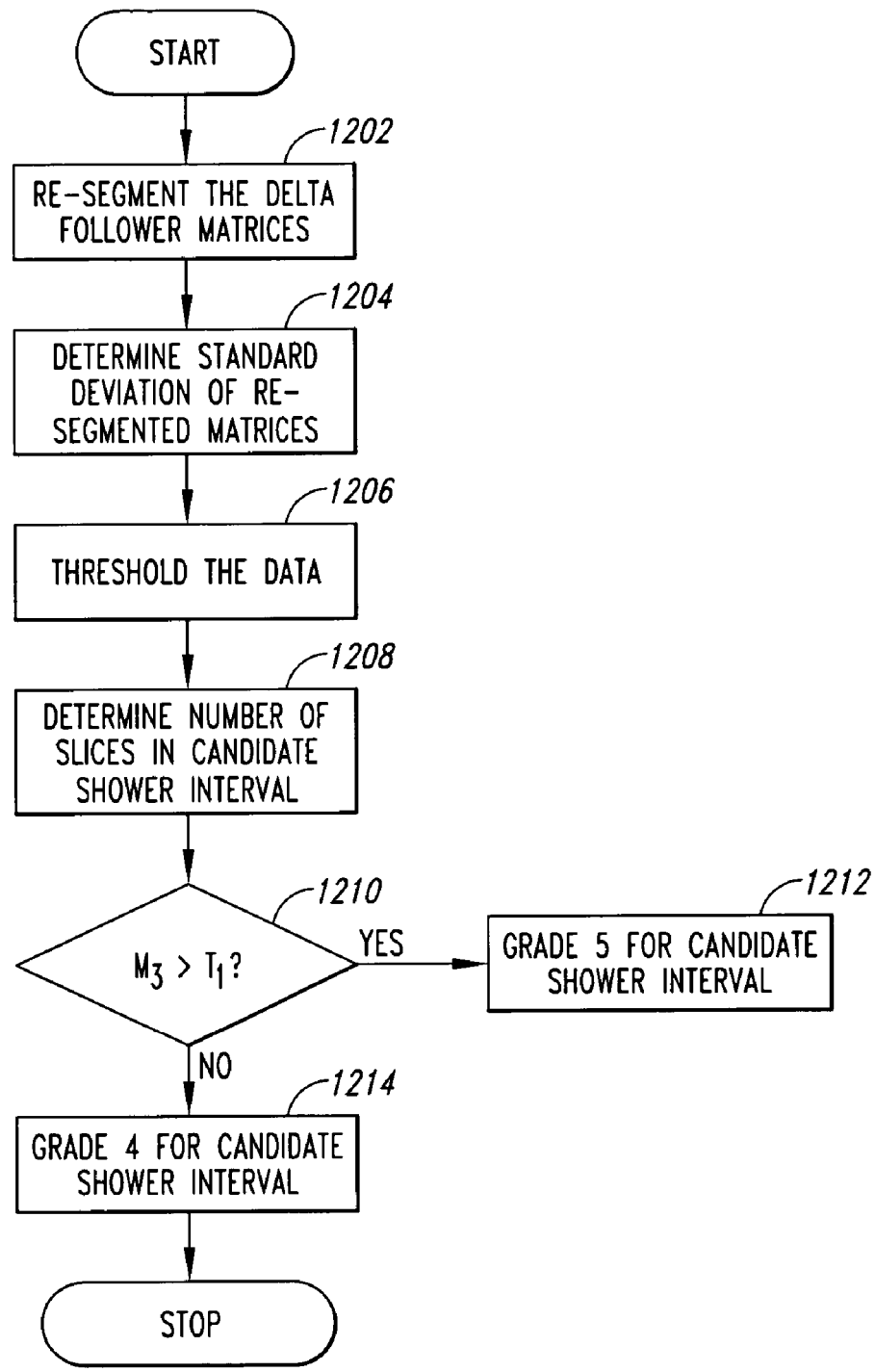
FIG. 12 is a flow diagram for processing data in FIG. 10 according to an alternative embodiment of the present invention.

In an alternative embodiment, the grading/counting algorithm of FIG. 10 is modified to include an additional algorithm for distinguishing between grade 4 and grade 5. The additional algorithm is described with respect to FIG. 12. At step 1202, the delta follower matrices $\Delta^L$, $\Delta^R$ constructed at step 1108 (FIG. 11) are re-segmented into a series of non-overlapping windows which have size of $m_0=17$ rows and $m_1=100$ columns. This is accomplished by taking the total number of columns in the $\Delta^L$, $\Delta^R$ matrices and dividing by $m_2=75$ to get the number of columns, $m_1=100$, in each non-overlapping sub-matrix. Each sub-matrix is reshaped into a column vector with the same number of total points of $m_0 \cdot m_1 = 1{,}700$. The $m_1=100$ resulting column vectors in a given sub-matrix are concatenated to build a matrix Δ' having $m_0 \cdot m_1 = 1{,}700$ rows and $m_2=75$ columns for each channel.

At step 1204, the standard deviation of each column of Δ' is calculated to construct a row vector η having 75 values. At step 1206, the domains of the signal η for which the signal exceeds a threshold of $T_0=5$ are found. Let $i_0$ indicate the index of the point where $\eta(i_0) < T_0 < \eta(i_0+1)$, and $i_1$ indicate the first index beyond $i_0$ where $\eta(i_1) > T_0 > \eta(i_1+1)$. At step 1208, the number of slices in the shower interval is equal to $m_3=(i_1-i_0+1) \cdot m_1$. At steps 1210, if $m_3 > T_1$ where $T_1=750$ slices, then a shower of grade 5 or higher is reported for the interval between the points $i_0$ and $i_1$ at step 1212. Otherwise, a shower of grade 4 is reported for the interval between the points $i_0$ and $i_1$ at step 1214.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for grading signals from microemboli in blood flow, the blood flow monitored using a Doppler ultrasound system, the method comprising:
   for a period of monitoring and a background period, extracting Doppler shift signals from echo signals resulting from ultrasound delivered to a region in which blood flow is detected;
   calculating signal-to-background data from the Doppler shift signals from the period of monitoring and the background period;
   partitioning the signal-to-background data into sub-periods having corresponding portions of the signal-to-background data;
   calculating correlative data from the signal-to-background data for a plurality of sub-periods; and
   categorizing the signals from microemboli in blood flow into one of at least two grades based at least in part on the correlative data.

2. The method of claim 1 wherein calculating signal-to-background data from the Doppler shift signals comprises:
   calculating mean background power for a depth range from the Doppler shift signals from the background period;
   calculating Doppler signal power values for the depth range over the period of monitoring from the Doppler shift signals from the period of monitoring; and
   dividing the Doppler signal power values by the mean background power for corresponding depths of the depth range.

3. The method of claim 2 wherein determining from the signal-to-background data the presence of microemboli in the blood flow during the period of monitoring comprises:
   identifying the signal-to-background data representing a signal-to-background ratio greater than a threshold value.

4. The method of claim 1 wherein categorizing the signals from microemboli in blood flow into one of at least two grades based at least in part on the correlative data comprises:
   summing the correlative data; and
   categorizing the signals from microemboli in blood flow into one of at least two grades based at least in part on the sum of the correlative data.

5. The method of claim 1 wherein delivering ultrasound to a region in which blood flow is present comprises:
   delivering ultrasound from first and second ultrasound probes for bilateral monitoring of the region;
   wherein extracting, calculating, and determining are performed for echo signals resulting from the ultrasound delivered by the respective ultrasound probes to provide decibel values for each of the probes;
   calculating beam power for the ultrasound delivered by each probe; and
   the value related to the power for the microemboli is provided by weighting the decibel values for each of the probes in accordance with the beam power calculated for each probe.

6. The method of claim 1 wherein categorizing the signals from microemboli in blood flow comprises:
   categorizing the signals from microemboli in blood flow into at least one high grade in response to the value being greater than or equal to a threshold value; and
   in response to the value being less than the threshold value, the method further comprising:

calculating a count value corresponding to a number of signals from microemboli in the blood flow; and categorizing the signals from microemboli in blood flow into one of a plurality of grades based on the count value.

7. The method of claim 1 wherein categorizing the signals from microemboli in blood flow into one of at least two grades comprises categorizing the signals from microemboli in blood flow into a grade of a six-level logarithmic scale.

8. The method of claim 1, further comprising:

in the event the value is greater than the threshold value, determining whether the signals from microemboli in the blood flow over a period of monitoring is graded as a first high grade or a second high grade for sub-periods of the period of monitoring.

9. The method of claim 1 wherein calculating correlative data from the signal-to-background data for a plurality of sub-periods comprises calculating correlative data from the signal-to-background data for a plurality of adjacent sub-periods.

10. The method of claim 1 further comprising storing in memory data indicative of the grade for the signals from microemboli.

11. A method for categorizing microemboli in blood flow monitored using a Doppler ultrasound system, the method comprising:

assessing a power value for the microemboli in the blood flow during a period of monitoring;

in response to the power value being greater than or equal to a threshold value, categorizing the microemboli in the blood flow based on the power value; and in response to the power value being less than the threshold value, counting a number of microemboli during at least a portion of the period of monitoring and categorizing the microemboli based on the number.

12. The method of claim 11 wherein assessing a power value for the microemboli in the blood flow during a period of monitoring comprises assessing a power value for bubble emboli in cerebral blood flow during the period of monitoring.

13. The method of claim 12 wherein categorizing the microemboli in the blood flow based on the power value comprises categorizing the bubble emboli in a grade for a grading scale related to functional conductance of patent foramen ovale.

14. A Doppler ultrasound system, comprising:

a probe having an ultrasound transducer;

a transmitter circuit operably coupled to the ultrasound transducer and configured to generate drive signals for driving the ultrasound transducer to deliver ultrasound;

a receiver circuit operably coupled to the ultrasound transducer and configured to receive echo signals detected by the ultrasound transducer and generate in response thereto echo data representative of the echo signals; and a processing system operably coupled to the transmitter and receiver circuits and configured to control the transmit circuit in generating drive signals for the ultrasound transducer and configured to process the echo data from the receiver circuit and extract therefrom Doppler shift signals represented by Doppler shift data for a period of monitoring and a background period, the processing system further configured to process the Doppler shift data to calculate signal-to-background data, partition the signal-to-background data into sub-periods having corresponding portions of the signal-to-background data, calculate correlative data from the signal-to-background data for a plurality of sub-periods, and categorize the signals from microemboli in blood flow into one of at least two grades based at least in part on the correlative data.

15. The system of claim 14 wherein the processing system configured to calculate signal-to-background data from the Doppler shift signals comprises a processor configured to calculate mean background power for a depth range from the Doppler shift signals from the background period, calculate Doppler signal power values for the depth range over the period of monitoring from the Doppler shift signals from the period of monitoring, and divide the Doppler signal power values by the mean background power for corresponding depths of the depth range.

16. The system of claim 14 wherein the processing system configured to process the Doppler shift data to categorize the signals from microemboli in blood flow into one of at least two grades based at least in part on the correlative values comprises a processor configured to sum the correlative data, and categorize the signals from microemboli in blood flow into one of at least two grades based at least in part on the sum of the correlative values.

17. The system of claim 14 wherein the probe comprises a first probe, the transmitter circuit comprises a first transmitter circuit, and the receiver circuit comprises a first receiver circuit, and the system further comprises a second probe having an ultrasound transducer, a second transmitter circuit operably coupled to the ultrasound transducer of the second probe, and a second receiver circuit operably coupled to the ultrasound transducer of the second probe, the processing system comprises a processor configured to control the first and second transmit and receive circuits to deliver ultrasound from first and second probes for bilateral monitoring of a region, and the extracting, calculating, and determining are performed for echo signals resulting from the ultrasound delivered by the respective ultrasound probes to provide decibel values for each of the probes, the processor further configured to calculate beam power for the ultrasound delivered by each probe and calculate the value related to the power for the microemboli by weighting the decibel values for each of the probes in accordance with the beam power calculated for each probe.

18. The system of claim 14 wherein the processing system configured to categorize the signals from microemboli in blood flow comprises a processor configured to categorize the signals from microemboli in blood flow into at least one high grade in response to the value being greater than or equal to a threshold value and in response to the value being less than the threshold value, the processor is further configured to calculate a count value corresponding to a number of signals from microemboli in the blood flow and categorize the signals from microemboli in blood flow into one of a plurality of grades based on the count value.

19. The system of claim 14 wherein the processing system comprises a processor configured to determine whether the signals from microemboli in the blood flow over a period of monitoring is graded as a first high grade or a second high grade for sub-periods of the period of monitoring in the event the value is greater than a threshold value.

20. The system of claim 14 wherein the processing system configured to calculate correlative data from the signal-to-background data for a plurality of sub-periods comprises a processor configured to calculate correlative data from the signal-to-background data for a plurality of adjacent sub-periods.

21. A processing system for a Doppler ultrasound system having a probe having an ultrasound transducer, transmit beam forming circuits, and receive beam forming circuits, the processing system comprising:

a processor configured to extract Doppler shift signals from echo signals detected by the beam forming circuits and further configured to process the Doppler shift signals to assess a power value for microemboli in blood flow monitored by the Doppler ultrasound system during a period of monitoring and categorize microemboli in blood flow based on the power value in response to the power value being greater than or equal to a threshold value, the processor further configured to count a number of microemboli in blood flow during at least a portion of the period of monitoring and categorize the microemboli in blood flow based on the number in response to the power value being less than the threshold value.

22. The system of claim 21 wherein the processor configured to assess a power value for microemboli in the blood flow during a period of monitoring comprises a processor configured to assess a power value for bubble emboli in cerebral blood flow during the period of monitoring.

23. The system of claim 22 wherein the processor is configured to categorize the bubble emboli in a grade for a grading scale related to functional conductance of patent foramen ovale.

* * * * *

UNITED STATES PATENT AND TRADEMARK OFFICE
CERTIFICATE OF CORRECTION

| | | |
|---|---|---|
| PATENT NO. | : 7,771,358 B2 | Page 1 of 1 |
| APPLICATION NO. | : 11/134862 | |
| DATED | : August 10, 2010 | |
| INVENTOR(S) | : Mark A. Moehring et al. | |

It is certified that error appears in the above-identified patent and that said Letters Patent is hereby corrected as shown below:

| Column, Line | Reads | Should Read |
|---|---|---|
| Column 6, Line 35 | "the prove 112" | --the probe 112-- |
| Column 9, Line 40 | "and "I" for the left" | --and "L" for the left-- |
| Column 9, Line 42 | "the right channel is" | --the left channel is-- |

Signed and Sealed this
Thirteenth Day of March, 2012

David J. Kappos
*Director of the United States Patent and Trademark Office*